US011203602B2

(12) United States Patent
Piscopio

(10) Patent No.: US 11,203,602 B2
(45) Date of Patent: Dec. 21, 2021

(54) THIOESTER PRODRUGS OF MACROCYCLES AS INHIBITORS OF HISTONE DEACETYLASES

(71) Applicant: OnKure, Inc., Boulder, CO (US)

(72) Inventor: Anthony D. Piscopio, Longmont, CO (US)

(73) Assignee: OnKure, Inc., Boulder, CO (US)

( * ) Notice: Subject to any disclaimer, the term of this patent is extended or adjusted under 35 U.S.C. 154(b) by 51 days.

(21) Appl. No.: 16/303,217

(22) PCT Filed: May 18, 2017

(86) PCT No.: PCT/US2017/033316
§ 371 (c)(1),
(2) Date: Nov. 20, 2018

(87) PCT Pub. No.: WO2017/201278
PCT Pub. Date: Nov. 23, 2017

(65) Prior Publication Data
US 2020/0317693 A1 Oct. 8, 2020

Related U.S. Application Data

(60) Provisional application No. 62/339,772, filed on May 20, 2016.

(51) Int. Cl.
| C07D 513/08 | (2006.01) |
| A61K 45/06 | (2006.01) |
| A61K 38/15 | (2006.01) |
| C07K 11/02 | (2006.01) |

(52) U.S. Cl.
CPC ............ *C07D 513/08* (2013.01); *A61K 38/15* (2013.01); *C07K 11/02* (2013.01); *A61K 45/06* (2013.01)

(58) Field of Classification Search
None
See application file for complete search history.

(56) References Cited

U.S. PATENT DOCUMENTS

| 8,933,195 B2 | 1/2015 | Jiang et al. |
| 2007/0129290 A1 | 6/2007 | Or et al. |
| 2014/0243501 A1 | 8/2014 | Jiang et al. |
| 2015/0010541 A1 | 1/2015 | Liu et al. |

FOREIGN PATENT DOCUMENTS

| JP | 2009519224 A | 5/2009 |
| WO | 2015/027959 A1 | 3/2015 |
| WO | 2015/183897 A1 | 12/2015 |

OTHER PUBLICATIONS

Haberland. Nature Reviews: Genetics, 2009, 10, 32-42 (Year: 2009).*

Chinese Office Action for Chinese Application No. 201780002181.3, dated Sep. 30, 2020, with translation, 12 pages.
International Search Report issued in corresponding International Patent Application No. PCT/US2017/033316 dated Aug. 16, 2017.
Written Opinion issued in corresponding International Patent Application No. PCT/US2017/033316 dated Aug. 16, 2017.
Benelkebir, H., et al. "Total Synthesis of Largazole and Analogues: HDAC Inhibition, Antiproliferative Activity and Metabolic Stability," Jun. 15, 2011, pp. 3650-3658, vol. 19(12), Bioorganic & Medicinal Chemistry.
Taiwan Office Action with Search Report for Taiwan Application No. 106116785, dated Jun. 20, 2020, 7 pages.
Japanese Notice of Reasons for Rejection for Japanese Application No. 2020-071408, dated Mar. 16, 2021 with translation, 4 pages.
Taiwan Office Action for Taiwan Application No. 106116785, dated Oct. 27, 2020 with translation, 7 pages.
Hang et al., "Chemoselective Approaches to Glycoprotein Assembly", Accounts of Chemical Research, 2001, vol. 34, No. 9, pp. 727-736.
Johnstone, "Histone-Deacetylase Inhibitors: Novel Drugs For The Treatment of Cancer", Nature Reviews, 2002, vol. 1, pp. 287-299.
Lemieux et al., "Chemoselective Ligation Reactions with Proteins, Oligosaccharides and Cells", Reviews, 1998, vol. 16, pp. 506-513.
Liu et al., "Anticolon Cancer Activity of Largazole, a Marine-Derived Tunable Histone Daecetylase Inhibitor", The Journal of Pharmacology and Experimental Therapeutics, 2010, vol. 335, No. 2, pp. 351-361.
Masuoka et al., "Spiruchostatins A and B, Novel Gene Expression-Enhancing Substances Produced by Pseudomonas sp.", Tetrahedron Letters, 2001, vol. 42, pp. 41-44.

(Continued)

*Primary Examiner* — Noble E Jarrell
(74) *Attorney, Agent, or Firm* — RatnerPrestia

(57) ABSTRACT

The present invention provides a novel macrocyclic prodrug compound of general Formula (I), a pharmaceutical composition comprising a compound of Formula (I), and a method for treating diseases mediated by HDAC enzymes by administering a compound of Formula (I), wherein $R^1$, $R^2$, $R^3$, $R^4$, $R^5$, $R^6$, $R^7$, $R^8$, $R^9$, $R^{10}$, $R^{11}$, A and Z are defined herein.

(I)

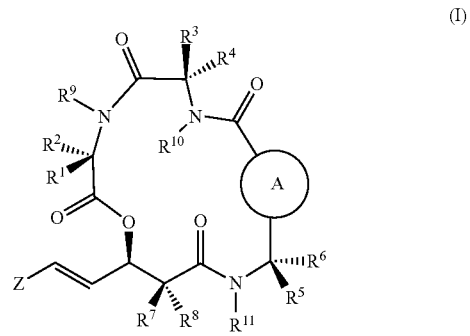

14 Claims, 5 Drawing Sheets

(56) References Cited

OTHER PUBLICATIONS

Moradei et al., "Histone Deacetylase Inhibitors: Latest Developments, Trends and Prospects", Curr. Med. Chem.—Anti Cancer Agents, 2005, vol. 5, pp. 529-560.

Nasveschuk et al., "A Concise Total Synthesis of Largazole, Solution Structure, and Some Preliminary Structure Activity Relationships", Organic Letters, 2008, vol. 10, No. 16, pp. 3595-3598.

Newkirk et al. "Discovery, Biological Activity, Synthesis and Potential Therapeutic Utility of Naturally Occurring Histone Deacetylase Inhibitors", Natural Products Reports, 2009, vol. 26, pp. 1293-1320.

Seiser et al., "Synthesis and Biological Activity of Largazole and Derivatives", Angew. Chern. Int. Ed., 2008, vol. 47, pp. 6483-6485.

Sisido, "Expanding the Genetic Code", Chemical Biology, 2007, pp. 271-295.

Somech et al., "Histone Deactylase Inhibitors—A New Tool To Treat Cancer", Cancer Treatment Reviews, 2004, vol. 3, pp. 461-472.

Ying et al., "Total Synthesis and Molecular Target of Largazole, a Histone Deacetylase Inhibitor", Journal of American Cancer Society, 2008, vol. 130, pp. 8455-8459.

Yoshida et al., "Structural Specificity for Biological Activity of Trichostatin A, A Specific Inhibitor of Mammalian Cell Cycle With Potent Differentiation-Inducing Activity in Friend Leukemia Cells", The Journal of Antibiotics, 1990, vol. XLIII, No. 9, pp. 1101-1106.

Zeng et al., "Total Synthesis and Biological Evaluation of Largazole and Derivatives with Promising Selectivity for Cancers Cells", Organic Letters, vol. 12. No. 6, pp. 1368-1371.

Chinese Office Action for Chinese Application No. 201780002181.3, dated Aug. 24, 2021, with translation, 12 pages.

\* cited by examiner

THIOESTER PRODRUGS OF MACROCYCLES AS INHIBITORS OF HISTONE DEACETYLASES

TECHNICAL FIELD

The present invention relates to prodrugs of macrocyclic histone deacetylase inhibitors, their synthesis and their methods of use.

BACKGROUND OF THE INVENTION

Largazole (1) is a highly functionalized macrocyclic depsipeptide isolated

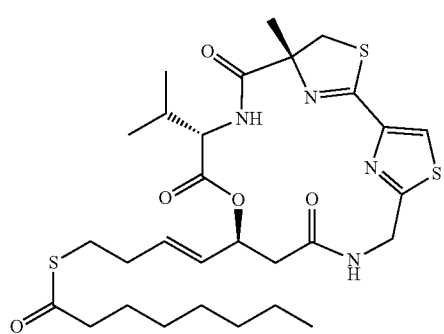

(1)

from the cyanobacterium *Symploca* sp. (Taori, K., et al., J. Am. Chem. Soc. 2008, 130, 1806-1807; Ying, Y., et al., J. Am. Chem. Soc. 2008, 130, 8455-8459). Largazole exhibits exceptionally potent and selective biological activity, with two- to ten-fold differential growth inhibition in a number of transformed and non-transformed human and murine-derived cell lines. The superior selectivity of largazole against cancer cells has prompted particular interest in its mode of action and its value as a potential lead compound for discovering and developing novel cancer chemotherapeutic agents.

The 3-hydroxy-7-mercaptohept-4-enoic acid moiety in largazole is an essential functionality in several cytotoxic natural products, including FK228 (FR901228) (Fujisawa Pharmaceutical Co., Ltd., Jpn. Kokai Tokkyo Koho JP03141296, 1991; Ueda, H., et al., J. Antibiot. 1994, 47, 301; Shigematsu, N., et al., J. Antibiot. 1994, 47, 311; Ueda, H., et al., J. Antibiot. 1994, 47, 315) (see FIG. 1); FR901375 (Fujisawa Pharmaceutical Co., Ltd., Jpn. Kokai Tokkyo Koho JP03141296, 1991; Ueda, H., et al., J. Antibiot. 1994, 47, 301; Shigematsu, N., et al., J. Antibiot. 1994, 47, 311; Ueda, H., et al., J. Antibiot. 1994, 47, 315); and Spiruchostatins A and B (Masuoka, Y., et al., Tetrahedron Lett. 2001, 42, 41), all of which are known as histone deacetylase inhibitors (HDACi) (Townsend, P. A., et al., 2007, "The bicyclic depsipeptide family of histone deacetylase inhibitors", Chemical Biology; Schreiber, S. L., et al., Eds. Wiley-VCH Verlag GmbH & Co. 693-720).

The histone deacetylase enzymes (HDACs) are zinc metallo-enzymes that catalyze the hydrolysis of acetylated lysine residues in chromatin and, thereby, regulate transcription in eukaryotic cells (Somech, R., et al., Cancer Treat. Rev. 2004, 30, 461; Miller, T. A. et al., J. Med. Chem. 2003, 46, 5097; Moradei, O., et al., Curr. Med. Chem.: Anti-Cancer Agents 2005, 5, 529; Bolden, J. E., et al., Nat. Rev. Drug Discovery 2006, 5, 769). Dysfunction of the HDACs is often associated with a variety of human tumors (Marks and Breslow 2007). As a result, selective inhibition has recently become a major area of research in cancer chemotherapy (Minucci, S., et al., Nature Rev. Cancer 2006, 6, 38). To date, eighteen HDACs have been identified and are generally divided into four classes based on sequence homology to yeast counterparts (Taunton, J., et al., Science 1996, 272, 408; Grozinger, C. M., et al., Proc. Nat. Acad. Sci. USA 1999, 96, 4868; Johnstone, R. W., Nature Rev. Drug Disc. 2002, 1, 287). With respect to cancer therapy, there is an emerging consensus that Class I HDACs are clinically relevant, and that the undesirable toxicity associated with the first generation of HDAC inhibitors may be related to class indiscriminancy. As a result, programs have been initiated that are aimed at the synthesis and modification of peptide- and depsipeptide-based HDACs with the objective of optimizing structures for class- and isoform-specific inhibition.

The three natural substances FK228, FR901375 and spiruchostatin are all activated in vitro and in vivo by reductive cleavage of a disulfide bond to expose the free sulfhydryl residue of the pendant (S)-3-hydroxy-7-mercaptohept-4-enoic acid moiety that coordinates to the active-site $Zn^{2+}$ residue of the HDACs resulting in a potent inhibitory effect (Yoshida, M., et al., J. Biol. Chem. 1990, 265, 17174; Yoshida, M., et al., J. Antibiot. 1990, 43, 1101). Given that largazole contains this well-known $Zn^{2+}$ binding arm, it is reasonable to assume that largazole is a pro-drug activated in vitro by hydrolytic removal of the octanoate residue by cellular lipases and/or esterases, and activated in-vivo by cellular and/or circulating plasma esterases and/or lipases, to produce the putative cytotoxic species (2) (the "largazole thiol"). It has previously been demonstrated that thioester analogues of FK228 retain their

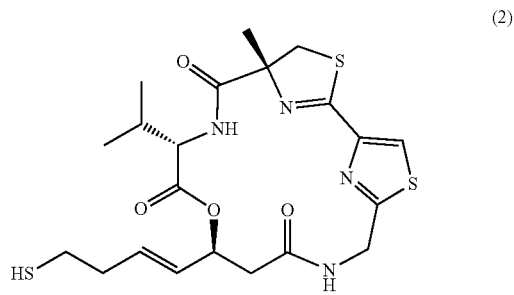 [SMILES: CC(C)[C@@H]1NC(=O)[C@]2(C)CSC(=N2)c2csc(n2)CNC(=O)C[C@@H](/C=C/CCS)OC1=O]

(2)

anti-proliferative activity in cell-based assays (WO 2007/061939; Yurek-George, A., et al., J. Med. Chem. 2007, 50, 5720).

The octanoate thioester prodrug residue is a unique and distinguishing feature of largazole and underscores the level of chemical diversity offered by nature. In addition, the U.S. Pharmacopeia is replete with examples of naturally occurring drugs and their corresponding unnatural derivatives. While many compounds exhibit potency and selectivity against particular biological targets, the physiochemical properties of these compounds often render them problematic for development in a pharmaceutical setting. As a result, strategies have evolved for creating analogous compounds in the laboratory that retain the biological potency of the parent compound but are more amenable for clinical development and commercialization (Rautio, J., Kumpulainen, H., Heimbach, T., Oliyai, R., Oh, D., Jarvinen, T., and Savolainen, J., Prodrugs: design and clinical applications, Nat Rev Drug Discov. 2008, 7(3): 255-270).

Described herein are prodrug derivatives of macrocyclic histone deacetylase inhibitors that present attractive alternatives to octanoate thioesters based on their unexpectedly superior physiochemical properties.

SUMMARY OF THE INVENTION

The present invention describes novel macrocyclic prodrug compounds, pharmaceutical compositions comprising them and novel processes for their preparation and therapeutic use. In an aspect of the invention, the macrocyclic prodrugs described herein inhibit HDAC. In an exemplary application, the prodrugs act as antiproliferation agents for cancer therapy and exhibit selectivity in targeting various HDACs.

One aspect of the present invention is a prodrug compound of Formula (I)

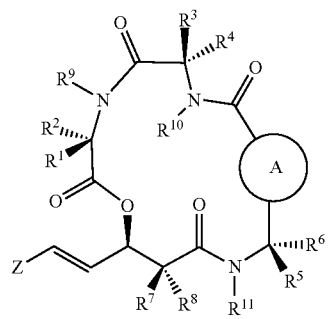

(I)

wherein:
"A" is aryl or heteroaryl, optionally substituted with one or more groups selected from the group consisting of $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

Z is —(CH$_2$)$_n$SR$_{12}$;

$R_1$ and $R_2$ are each independently H, halo, $C_1$-$C_{10}$ alkyl, $C_3$-$C_{10}$ cycloalkyl or $C_3$-$C_{10}$ heterocycloalkyl,
or $R_1$ and $R_2$ together, or one of $R_1$ and $R_2$ together with $R_9$ forms a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_3$ and $R_4$ are each independently H, halo, $C_1$-$C_{10}$ alkyl, $C_3$-$C_{10}$ cycloalkyl or $C_3$-$C_{10}$ heterocycloalkyl,
or $R_3$ and $R_4$ together, or one of $R_3$ and $R_4$ together with $R_{10}$ forms a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$, —CONR$_{20}$R$_{22}$ and —S(O)$_m$R$_{20}$;

$R_5$ and $R_6$ are each independently H, halo, $C_1$-$C_{10}$ alkyl, $C_3$-$C_{10}$ cycloalkyl or $C_3$-$C_{10}$ heterocycloalkyl,
or $R_5$ and $R_6$ together, or one of $R_5$ and $R_6$ together with $R_{11}$ forms a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_7$ and $R_8$ are each independently H, halo, $C_1$-$C_{10}$ alkyl, $C_3$-$C_{10}$ cycloalkyl or $C_3$-$C_{10}$ heterocycloalkyl,
or $R_7$ and $R_8$ together form a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_9$ is H, $C_1$-$C_{10}$ alkyl, $C_3$-$C_{10}$ cycloalkyl, or $C_3$-$C_{10}$ heterocycloalkyl,
or $R_9$ together with one of $R_1$ and $R_2$ forms a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_{10}$ is H, $C_1$-$C_{10}$ alkyl, $C_3$-$C_{10}$ cycloalkyl or $C_3$-$C_{10}$ heterocycloalkyl,
or $R_{10}$ together with one of $R_3$ and $R_4$ forms a $C_3$-$C_{10}$ cycloalkyl or $C_3$-$C_{10}$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_{11}$ is H, $C_1$-$C_{10}$ alkyl, $C_3$-$C_{10}$ cycloalkyl or $C_3$-$C_{10}$ heterocycloalkyl,
or $R_{11}$ together with one of $R_5$ and $R_6$ forms a $C_3$-$C_8$ cycloalkyl or $C_3$-$C_8$ heterocycloalkyl,
wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_8$ alkyl, $C_3$-$C_8$ cycloalkyl, $C_3$-$C_8$ heterocycloalkyl, aryl, heteroaryl, halo, hydroxyl, —CN, —COOH, —CF$_3$, —OCH$_2$F, —OR$_{20}$, —NR$_{20}$R$_{22}$, —NCOR$_{20}$R$_{22}$ and —CONR$_{20}$R$_{22}$;

$R_{12}$ is C(O)CR$_{20}$R$_{22}$NR$_{20}$R$_{22}$, C(O)R$_{23}$ or C(O)(CH$_2$)$_q$CO$_2$H;

$R_{20}$ and $R_{22}$ are each independently H, $C_1$-$C_{10}$ alkyl, $C_3$-$C_{10}$ cycloalkyl, $C_3$-$C_{10}$ heterocycloalkyl, aryl or heteroaryl, or taken together, $R_{20}$ and $R_{22}$ form a 3-7 membered optionally substituted carbocyclic or heterocyclic ring;

$R_{23}$ is an optionally substituted aryl or heteroaryl ring;

n=1 to 5 (such as 1 to 4, such as 1 to 3, such as 1 or 2);

m=1 or 2; and q=2 to 8, or a pharmaceutically acceptable salt, solvate, or stereoisomer thereof.

Another aspect of the present invention is a prodrug compound of Formula (II)

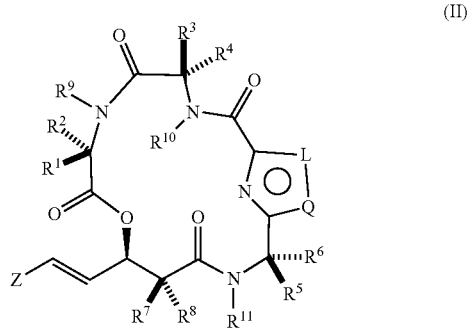

(II)

wherein:

L and Q are independently S, O, N, or $CR_{26}$;

$R_{26}$ is independently H, halo, $C_1$-$C_{10}$ alkyl, $C_3$-$C_{10}$ cycloalkyl, $C_3$-$C_{10}$ heterocycloalkyl, aryl or heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_1$, $R_2$, $R_3$, $R_4$, $R_5$, $R_6$, $R_7$, $R_8$, $R_9$, $R_{10}$, $R_{11}$ and Z are as described above, or a pharmaceutically acceptable salt, solvate or stereoisomer thereof.

Another aspect of the present invention is a prodrug compound of Formula (III)

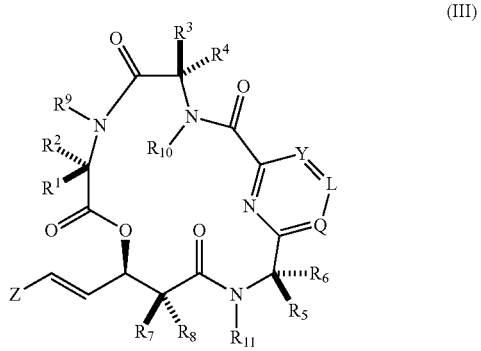

(III)

wherein:

L, Q and Y are independently S, O, N, or $CR_{26}$;

$R_{26}$ is independently H, halo, $C_1$-$C_{10}$ alkyl, $C_3$-$C_{10}$ cycloalkyl, $C_3$-$C_{10}$ heterocycloalkyl, aryl or heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_1$, $R_2$, $R_3$, $R_4$, $R_5$, $R_6$, $R_7$, $R_8$, $R_9$, $R_{10}$, $R_{11}$ and Z are as described above, or a pharmaceutically acceptable salt, solvate or stereoisomer thereof.

In an exemplary embodiment, the prodrug compound of Formula (I) is (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof. In a particular embodiment, the pharmaceutically acceptable salt thereof is a hydrochloride salt.

In an exemplary embodiment, the prodrug compound of Formula (I) is (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof. In a particular embodiment, the pharmaceutically acceptable salt thereof is a hydrochloride salt.

In a particular embodiment, the prodrug compound of Formula (I) is (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate or a solvate or stereoisomer thereof.

In a particular embodiment, the prodrug compound of Formula (I) is (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof.

In a particular embodiment, the prodrug compound of Formula (I) is (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof.

In a particular embodiment, the prodrug compound of Formula (I) is S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate or a pharmaceutically acceptable salt, solvate or stereoisomer thereof.

In a particular embodiment, the prodrug compound of Formula (I) is S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate or a pharmaceutically acceptable salt, solvate or stereoisomer thereof.

In a particular embodiment, the prodrug compound of Formula (I) is 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid or a pharmaceutically acceptable salt, solvate or stereoisomer thereof.

Another aspect of the present invention is a pharmaceutical composition comprising one or more of the prodrug compounds of Formula (I), (II) and (III) or a pharmaceutically acceptable salt thereof, and a pharmaceutically acceptable carrier.

In an exemplary embodiment, the pharmaceutical composition comprises (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but- 3-en-1-yl) 2-amino-3-methylbutanethioate or a pharmaceutically acceptable salt, solvate or stereoisomer thereof, and a pharmaceutically acceptable carrier. In a particular embodiment, the pharmaceutically acceptable salt is a hydrochloride salt.

In an exemplary embodiment, the pharmaceutical composition comprises (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof, and a pharmaceutically acceptable carrier. In a particular embodiment, the pharmaceutically acceptable salt is a hydrochloride salt.

In an exemplary embodiment, the pharmaceutical composition comprises (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate or a solvate or stereoisomer thereof, and a pharmaceutically acceptable carrier.

In an exemplary embodiment, the pharmaceutical composition comprises (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof, and a pharmaceutically acceptable carrier.

In an exemplary embodiment, the pharmaceutical composition comprises (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof, and a pharmaceutically acceptable carrier.

In an exemplary embodiment, the pharmaceutical composition comprises S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate or a pharmaceutically acceptable salt, solvate or stereoisomer thereof, and a pharmaceutically acceptable carrier.

In an exemplary embodiment, the pharmaceutical composition comprises S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate or a pharmaceutically acceptable salt, solvate or stereoisomer thereof, and a pharmaceutically acceptable carrier.

In an exemplary embodiment, the pharmaceutical composition comprises 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid or a pharmaceutically acceptable salt, solvate or stereoisomer thereof, and a pharmaceutically acceptable carrier.

In an exemplary embodiment, the pharmaceutical composition consists of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof, and a pharmaceutically acceptable carrier. In a particular embodiment, the pharmaceutically acceptable salt is a hydrochloride salt.

In an exemplary embodiment, the pharmaceutical composition consists of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof, and a pharmaceutically acceptable carrier. In a particular embodiment, the pharmaceutically acceptable salt is a hydrochloride salt.

In an exemplary embodiment, the pharmaceutical composition consists of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate or a solvate or stereoisomer thereof, and a pharmaceutically acceptable carrier.

In an exemplary embodiment, the pharmaceutical composition consists of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof, and a pharmaceutically acceptable carrier.

In an exemplary embodiment, the pharmaceutical composition consists of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof, and a pharmaceutically acceptable carrier.

In an exemplary embodiment, the pharmaceutical composition consists of S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate or a pharmaceutically acceptable salt, solvate or stereoisomer thereof, and a pharmaceutically acceptable carrier.

In an exemplary embodiment, the pharmaceutical composition consists of S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate or a pharmaceutically acceptable salt, solvate or stereoisomer thereof, and a pharmaceutically acceptable carrier.

In an exemplary embodiment, the pharmaceutical composition consists of 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid or a pharmaceutically acceptable salt, solvate or stereoisomer thereof, and a pharmaceutically acceptable carrier.

Another aspect of the present invention is a method of treating diseases mediated by HDAC enzymes, comprising administering to a subject in need thereof a therapeutically effective amount of one or more of the prodrug compounds of Formula (I), (II) and (III) described herein. A particular embodiment of the aforementioned method is a co-therapy, where one or more of the prodrug compounds of Formula (I), (II) and (III) are administered before, simultaneously with, or after administration of one or more other known therapeutic agents. In a particular embodiment, the known therapeutic agent is an anti-cancer agent.

In an exemplary embodiment, the method of treating diseases mediated by HDAC enzymes comprises administering to a subject in need thereof a therapeutically effective amount of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof. In a particular embodiment, the pharmaceutically acceptable salt is a hydrochloride salt.

In an exemplary embodiment, the method of treating diseases mediated by HDAC enzymes comprises administering to a subject in need thereof a therapeutically effective amount of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof. In a particular embodiment, the pharmaceutically acceptable salt is a hydrochloride salt.

In an exemplary embodiment, the method of treating diseases mediated by HDAC enzymes comprises administering to a subject in need thereof a therapeutically effective amount of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate or a solvate or stereoisomer thereof.

In an exemplary embodiment, the method of treating diseases mediated by HDAC enzymes comprises administering to a subject in need thereof a therapeutically effective amount of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof.

In an exemplary embodiment, the method of treating diseases mediated by HDAC enzymes comprises administering to a subject in need thereof a therapeutically effective amount of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof.

In an exemplary embodiment, the method of treating diseases mediated by HDAC enzymes comprises administering to a subject in need thereof a therapeutically effective amount of S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate or a pharmaceutically acceptable salt, solvate or stereoisomer thereof.

In an exemplary embodiment, the method of treating diseases mediated by HDAC enzymes comprises administering to a subject in need thereof a therapeutically effective amount of S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate or a pharmaceutically acceptable salt, solvate or stereoisomer thereof.

In an exemplary embodiment, the method of treating diseases mediated by HDAC enzymes comprises administering to a subject in need thereof a therapeutically effective amount of 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid or a pharmaceutically acceptable salt, solvate or stereoisomer thereof.

In an exemplary embodiment, (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof is administered as a co-therapy before, simultaneously with, or after administration of one or more other known therapeutic agents.

In an exemplary embodiment, (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate or a pharmaceutically acceptable salt, solvate or stereoisomer thereof is administered as a co-therapy before, simultaneously with, or after administration of one or more other known therapeutic agents.

In an exemplary embodiment, (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate or a solvate or stereoisomer thereof is administered as a co-therapy before, simultaneously with, or after administration of one or more other known therapeutic agents.

In an exemplary embodiment, (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof is administered as a co-therapy before, simultaneously with, or after administration of one or more other known therapeutic agents.

In an exemplary embodiment, (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate or a solvate or stereoisomer thereof is administered as a co-therapy before, simultaneously with, or after administration of one or more other known therapeutic agents.

In an exemplary embodiment, S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate or a pharmaceutically acceptable salt, solvate or stereoisomer thereof is administered as a co-therapy before, simultaneously with, or after administration of one or more other known therapeutic agents.

In an exemplary embodiment, S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate or a pharmaceutically acceptable salt, solvate or stereoisomer thereof is administered as a co-therapy before, simultaneously with, or after administration of one or more other known therapeutic agents.

In an exemplary embodiment, 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid or a pharmaceutically acceptable salt, solvate or stereoisomer thereof is administered as a co-therapy before, simultaneously with, or after administration of one or more other known therapeutic agents.

In an exemplary embodiment, the disease mediated by HDAC enzymes is cancer, such as colon cancer and/or breast cancer.

In a particular embodiment, the subject is a human.

BRIEF DESCRIPTION OF THE DRAWINGS

The following figures illustrate specific embodiments of the present invention but are not intended to otherwise limit the scope of the invention as described herein.

DETAILED DESCRIPTION

Definitions

Figure 1:
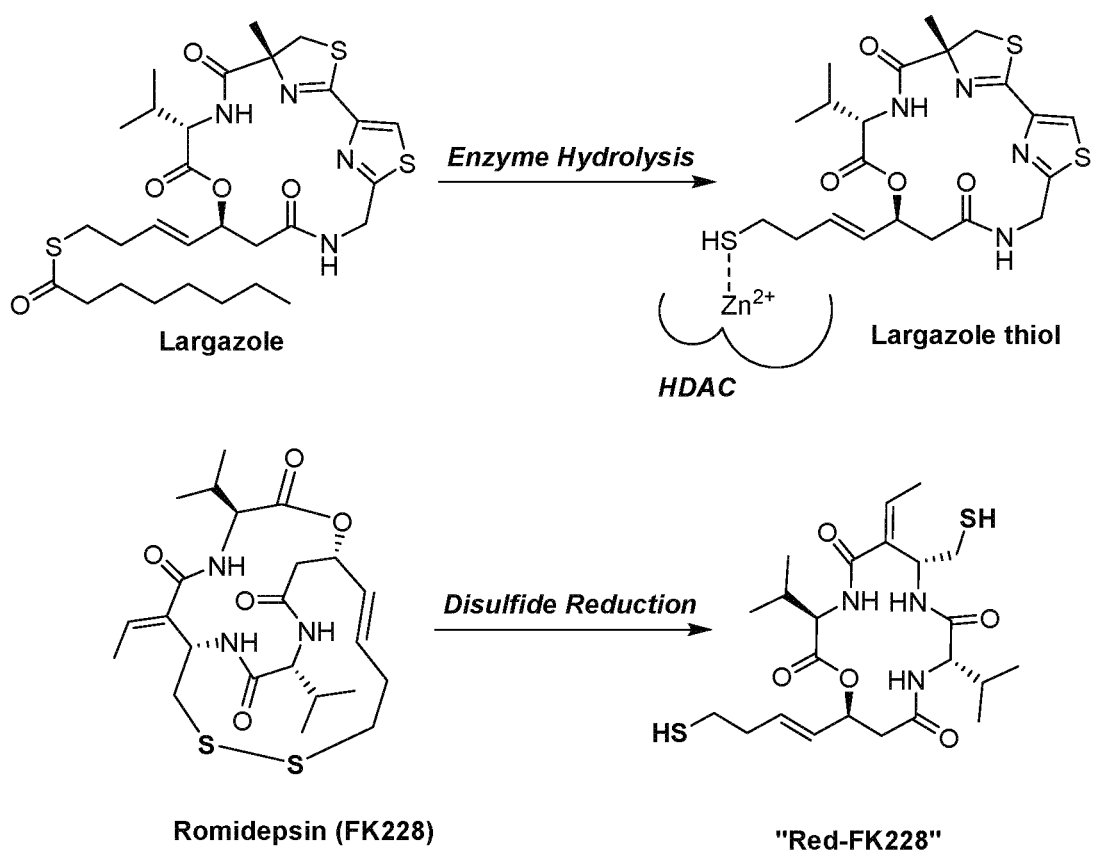
FIG. 1 depicts the activation of largazole and FK228 for carrying out HDAC inhibition. Largazole acts as a prodrug that upon hydrolysis is converted to the corresponding "active" thiol form, which deactivates HDAC by chelating zinc away from the active site of the enzyme. Similarly, reduction of the disulfide bond in FK228 liberates the "active" thiol form of the molecule that potently inhibits HDACs.

The term "substitute for" as used herein, refers to switching the administration of a first compound or drug to a subject for a second compound or drug to the subject.

The term "at risk for" as used herein, refers to a medical condition or set of medical conditions exhibited by a patient that may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which can be expressed as the ratio $LD_{50}/ED_{50}$. Compounds that exhibit large therapeutic indices are preferred. The data obtained from these cell culture assays and additional animal studies can be used in formulating a range of dosages for human use. The dosages of such compounds lie preferably within a range of circulating concentrations that include the $ED_{50}$ with little or no toxicity. The dosage varies within this range depending upon the dosage form employed, the sensitivity of the patient, and the route of administration.

The term "symptom" as used herein, refers to any observed subjective or objective evidence of disease or physical disturbance by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue body imaging scans and other medical testing results.

The term "disease" as used herein, refers to any impairment of the normal state of the living animal or one of its parts that interrupts or modifies the performance of the vital functions. Typically manifested by distinguishing signs and symptoms, it is usually a response to: i) environmental factors (such as malnutrition, industrial hazards, or climate); ii) specific infective agents (such as worms, bacteria, or viruses); iii) inherent defects of the organism (such as genetic anomalies); and/or iv) combinations of these factors.

The terms "reduce", "inhibit", "diminish", "suppress", "decrease", "prevent" and grammatical equivalents thereof (including "lower", "smaller", etc.) when used in reference to the expression of any symptom in an untreated subject relative to a treated subject, indicate that the quantity and/or magnitude of the symptoms in the treated subject is lower than in the untreated subject by any amount that is recognized as clinically relevant by any medically trained personnel. In exemplary embodiments, the quantity and/or magnitude of the symptoms in the treated subject are at least 10% lower than, at least 25% lower than, at least 50% lower than, at least 75% lower than or at least 90% lower than the quantity and/or magnitude of the symptoms in the untreated subject.

The term "inhibitory compound" as used herein, refers to any compound capable of interacting with (e.g., attaching, binding, etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering" as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" as used herein, is a human or animal and is not limited to hospitalization. For example, outpatients and persons in nursing homes may qualify as "patients." A patient may be a human or non-human animal of any age and therefore includes both adult and juveniles (i.e., children). It is not intended that the term "patient" connote a need for medical treatment. Therefore, a patient may voluntarily or involuntarily be subject to experimentation, whether clinical or in support of basic science studies.

The term "subject" as used herein, refers to a vertebrate, preferably a mammal, more preferably a primate, still more preferably a human. Mammals include, without limitation, humans, primates, wild animals, feral animals, farm animals, sports animals, and pets.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule considered a candidate as an inhibitory compound.

The term "protein" as used herein, refers to any of numerous naturally occurring extremely complex substances (such as an enzyme or antibody) that contain amino acid residues joined by peptide bonds, and which include carbon, hydrogen, nitrogen, oxygen, and typically sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically acceptable" or "pharmacologically acceptable", as used herein, refers to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, a polyol (such as, for example, glycerol, propylene glycol, and liquid polyethylene glycol, and the like), suitable mixtures thereof, vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a composition (such as, for example, a peptide composition) that has been subjected to treatment (e.g., for example, fractionation) to remove various other components, and which composition substantially retains its expressed biological activity.

The term "sample" as used herein, includes, for example, environmental and biological samples. Environmental samples include material from the environment such as soil and water. Biological samples include animal (e.g., human), fluids (e.g., blood, plasma and serum), solids (e.g., stool), tissue, liquid foods (e.g., milk), and solid foods (e.g., vegetables and fruits). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "biologically active" refers to any molecule having structural, regulatory or biochemical functions. For example, biological activity may be determined, for example, by restoration of wild-type growth in cells lacking protein activity. Cells lacking protein activity may be produced by many methods (e.g., point mutation and frameshift mutation). Complementation is achieved by transfecting cells that lack protein activity with an expression vector which expresses the protein, a derivative thereof, or a portion thereof.

The term "label" or "detectable label" is used herein to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, Texas Red®, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference in their entireties). The labels contemplated in the present invention may be detected by conventional methods. For example, radiolabels may be detected using photographic film or scintillation counters, and fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "conjugate" as used herein, refers to any compound that has been formed by the joining of two or more moieties.

A "moiety" or "group" as used herein, is any type of molecular arrangement designated by formula, chemical name, or structure. Within the context of certain embodiments, a conjugate comprises one or more moieties or chemical groups. This means that the formula of the moiety is substituted at some position in order to be joined and be a part of the molecular arrangement of the conjugate. However, although moieties may be directly covalently joined, it is not intended that two or more moieties must be directly covalently joined to each other. A linking group, a crosslinking group, or a joining group refers to any molecular arrangement that will connect moieties by covalent bonds such as, but not limited to, one or more amide group(s). Additionally, although the conjugate may be unsubstituted, the conjugate may have a variety of additional substituents connected to the linking groups and/or connected to the moieties.

A "polymer" or "polymer group" as used herein, refers to a chemical species or group composed of repeatedly linked moieties. Within certain embodiments, it is preferred that the number of repeating moieties is 3 or more or greater than 10. The linked moieties may be identical in structure or may vary in their moiety structures. A "monomeric polymer" or "homopolymer" is a polymer that contains the same repeating, asymmetric subunit. A "copolymer" is a polymer derived from two or more types of monomeric species (i.e., two or more different chemical asymmetric subunits). "Block copolymers" are polymers comprised of two or more species of polymer subunits linked by covalent bonds.

The term "substituted" as used herein, refers to at least one hydrogen atom of a molecular arrangement that is replaced with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocyclyl, and heterocycloalkyl, as well as, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —OR, —SR, —$SOR_a$, —$S(=O)_aR$, —$OS(=O)_2R_a$ and —$S(=O)OR_a$. In addition, the above substituents may be further substituted with one or more of the above substituents, such that the substituent comprises a substituted alkyl, substituted aryl, substituted arylalkyl, substituted heterocyclyl, or substituted heterocycloalkyl. $R_a$ and $R_b$ in this context may be the same or different and, independently, hydrogen, alkyl, haloalkyl, substituted alkyl, aryl, substituted aryl, arylalkyl, substituted arylalkyl, heterocyclyl, substituted heterocyclyl, heterocycloalkyl or substituted heterocycloalkyl.

The term "unsubstituted" as used herein, refers to any compound that does not contain extra substituents attached to the compound. An unsubstituted compound refers to the chemical makeup of the compound without extra substituents (e.g., no protecting group(s)). For example, unsubstituted proline is a proline amino acid even though the amino group of proline may be considered as disubstituted with alkyl groups.

The term "alkyl" as used herein, refers to any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 4 carbon atoms. The term "higher alkyl" has the same meaning as alkyl but contains from 5 to 10 carbon atoms. Representative saturated straight chain alkyls include, but are not limited to, methyl, ethyl, n-propyl, n-butyl, n-pentyl, n-hexyl, n-septyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl" as used herein, refers to any aromatic carbocyclic moiety such as, but not limited to, phenyl or naphthyl.

The term "arylalkyl" or "aralkyl" as used herein, refers to any alkyl having at least one alkyl hydrogen atom replaced with an aryl moiety (such as benzyl) but not limited to, —$(CH_2)_2$phenyl, —$(CH_2)_3$phenyl, —CH(phenyl)$_2$, and the like.

The term "halogen" as used herein, refers to any fluoro, chloro, bromo, or iodo moiety.

The term "haloalkyl" as used herein, refers to any alkyl having at least one hydrogen atom replaced with halogen, such as trifluoromethyl, and the like.

The term "heteroaryl" as used herein, refers to any aromatic heterocycle ring of 5- to 10-members and having at least one heteroatom selected from nitrogen, oxygen and sulfur, and containing at least 1 carbon atom, including, but not limited to, both mono and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl" as used herein, means any alkyl having at least one alkyl hydrogen atom replaced with a heteroaryl moiety, such as —CHpyridinyl, $CH_2$pyrimidinyl, and the like.

The term "heterocycle" or "heterocyclyl" or "heterocyclic ring" as used herein, refers to any 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl" as used herein, refers to any alkyl having at least one alkyl hydrogen atom replaced with a heterocycle, such as —$CH_2$morpholinyl, and the like.

The term "homocycle" or "cycloalkyl" as used herein, refers to any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino" as used herein, means at least one alkyl moiety attached through a nitrogen bridge (i.e., —N-(alkyl)$_n$, where n=1 or 2, such as alkylamino or dialkylamino) including, but not limited to, methylamino, ethylamino, dimethylamino, diethylamino, and the like.

The term "alkyloxy" or "alkoxy", as used herein, means any alkyl moiety attached through an oxygen bridge (i.e., —O-alkyl) such as, but not limited to, methoxy, ethoxy, and the like.

The term "alkylthio" as used herein, means any alkyl moiety attached through a sulfur bridge (i.e., —S-alkyl) such as, but not limited to, methylthio, ethylthio, and the like The term "alkenyl" as used herein, refers to an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" as used herein, refers to unbranched or branched hydrocarbon chain having one or more triple bonds therein. The triple bond of an alkynyl group can be unconjugated or conjugated to another unsaturated group. Suitable alkynyl groups include, but are not limited to ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents.

The term "salts" as used herein, refers to any salt that complexes with identified compounds contained herein. Examples of such salts include, but are not limited to, acid addition salts formed with inorganic acids (e.g., hydrochloric acid, hydrobromic acid, sulfuric acid, phosphoric acid, nitric acid, and the like) and salts formed with organic acids (e.g., acetic acid, oxalic acid, tartaric acid, succinic acid, malic acid, fumaric acid, maleic acid, ascorbic acid, benzoic acid, tannic acid, pamoic acid, alginic acid, polyglutamic acid, methanesulfonic acid (mesylate), benzenesulfonic acid (besylate), 4-nitrobenzene sulfonic acid (nosylate), 4-bromobenzene sulfonic acid (brosylate), toluensulfonic acid (tosylate), naphthalene sulfonic acid, naphthalene disulfonic acid, and polygalacturonic acid). Salt compounds can also be administered as pharmaceutically acceptable quaternary salts known by a person skilled in the art, which specifically include quaternary ammonium salts of the formula —NR, R', R''$^+$Z$^-$, wherein R, R' and R'' are independently hydrogen, alkyl, or benzyl, and Z is a counter ion, including, but not limited to, chloride, bromide, iodide, alkoxide, sulfonate (such as mesylate, besylate, nosylate, brosylate and tosylate), phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, sulfonate (such as mesylate, besylate, nosylate, brosylate and tosylate), phosphate, or carboxylate (such as benzoate, succinate, acetate, glycolate, maleate, malate, fumarate, citrate, tartrate, ascorbate, cinnamoate, mandeloate, and diphenylacetate).

As used herein, "reactive groups" refer to nucleophiles, electrophiles, or radically active groups, i.e., groups that react in the presence of radicals. A nucleophile is a moiety that forms a chemical bond to its reaction partner (the electrophile) by donating both bonding electrons. Electrophiles accept these electrons. Nucleophiles may take part in nucleophilic substitution, whereby a nucleophile becomes attracted to a full or partial positive charge on an element and displaces the group it is bonded to. Alternatively, nucleophiles may take part in substitution of carbonyl group. Carboxylic acids are often made electrophilic by creating succinyl esters and reacting these esters with aminoalkyls to form amides. Other common nucleophilic groups are thiolalkyls, hydroxylalkyls, primary and secondary amines, and carbon nucleophiles such as enols and alkyl metal complexes. Other preferred methods of ligating proteins, oligosaccharides and cells using reactive groups are disclosed (Lemieux and Bertozzi 1998, incorporated herein by reference in its entirety). In yet another preferred method, one provides reactive groups for the Staudinger ligation, i.e., "click chemistry" with an azide comprising moiety and alkynyl reactive groups to form triazoles. Michael additions of a carbon nucleophile enolate with an electrophilic carbonyl, or the Schiff base formation of a nucleophilic primary or secondary amine with an aldehyde or ketone may also be utilized. Other methods of bioconjugation are provided (Hang and Bertozzi 2001; and Kiick et al. 2002, both of which are incorporated by reference in their entireties).

The term "biocompatible" as used herein, refers to any material that does not elicit a substantial detrimental response in the host. There is always concern when a foreign object is introduced into a living body that the object will induce an immune reaction, such as an inflammatory response that will have negative effects on the host. In the context of this invention, biocompatibility is evaluated according to the application for which it was designed: for example, a bandage is regarded as biocompatible with the skin, whereas an implanted medical device is regarded as biocompatible with the internal tissues of the body. Preferably, biocompatible materials include, but are not limited to, biodegradable and biostable materials. A substantial detrimental response has not occurred if an implant comprising the material is in close association to its implant site within the host animal and the response is better than a tissue response recognized and established as suitable from materials provided in an ASTM. ASTM subcommittee F04.16 on Biocompatibility Test Methods has developed biocompatibility standards for medical and surgical materials and devices. For example, materials that are to be used in contact with the blood stream must be composed of materials that meet hemocompatibilty standards. One of these tests is for damage to red blood cells, which can result in hemolysis that is, rupturing of the cells, as described in F 756 Practice for Assessment of Hemolytic Properties of Materials, incorporated herein by reference.

As used herein, a "bioactive substance" refers to any of a variety of chemical moieties and that binds with a biomolecule such as, but not limited to, peptides, proteins, enzymes, receptors, substrates, lipids, antibodies, antigens, and nucleic acids. In certain preferred embodiments, the bioactive substance is a biomolecule but it not intended that the bioactive substance be limited to biomolecules. In other preferred embodiments, the bioactive substances provide hydrophobic, hydrophilic or electrostatic interactions, such as polycarboxylic acids that are anionic at physiological pH. In other preferred embodiment, the alkaline growth factors (with isoelectric point above 7) are retained via favorable electrostatic interactions by the polycarboxylates, and subsequently released in a controlled and sustained manner.

"Cancer" is a term used for diseases in which abnormal cells divide without control and are able to invade other tissues. There are more than 100 different types of cancer. Most cancers are named for the organ or type of cell in which they start—for example, cancer that begins in the colon is called colon cancer; cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In one embodiment, the cancers contemplated for treatment herein include colon and breast cancers.

The terms "comprises" and "comprising" are intended to have the broad meaning typically ascribed to them in U.S. patent law and can mean "includes", "including" and the like.

An objective of the invention is a method for improving upon largazole's structure-activity relationships by creating prodrugs of largazole analogs and assessing their physiochemical properties with respect to aqueous solubility and ultimately in vivo activity in humans, particularly via oral dosing, using rodent xenograft and patient derived tumor models as surrogates for the human disease.

In 2008, largazole was isolated from a cyanobacterium of the genus *Symploca*, and named for its Key Largo location (Luesch et al., University of Florida). The compound demonstrates antiproliferative activity in the transformed mammary epithelial cell line MDA-MB231 with a $GI_{50}$ of 7.7 nM (Taori et al. 2008). In addition, largazole preferentially targets cancer over normal cells, which makes this marine substance an important synthetic target as well as a potentially valuable cancer chemotherapeutic (Taori et al. 2008). The first reported synthesis of largazole was completed by Luesch and co-workers (Ying et al. 2008b), followed by the Phillips group (Nasveschuk et al. 2008), the Cramer group (Seiser et al. 2008), the Williams group (Bowers et al. 2008), and the Ghosh group (Ghosh and Kulkami 2008). The molecular basis for its anticancer activity has been suggested to be histone deacetylases (HDAC) inhibition (Ying et al. 2008b).

HDAC inhibitors have been suggested as a new class of potent anti-cancer agents for the treatment of solid and hematological malignancies. Current inhibitors of HDACs, such as sodium butyrate, Trichostatin A (TSA), suberoylanilide hydroxamic acid (SAHA), FK228, and others may exhibit their anti-tumor effect by regulating genes and their protein products that are required for cell cycle arrest, DNA damage repair, free radical scavenging and apoptosis (Marks 2010). For example, SAHA has been approved for the treatment of advanced cutaneous T-cell lymphoma (Marks 2007). Several other HDAC inhibitors are presently in clinical trials for cancer treatment (Marks 2010).

The structure of largazole comprises a 16-membered macrocycle containing a 4-methylthiazoline fused to a thiazole ring and an octanoic thioester side chain, a unit rarely found in natural products (Taori et al. 2008; Newkirk et al. 2009). It has been postulated that it is the macrocyclic part of the compound that interacts with the surface of the HDAC protein, while the side chain would get inserted into HDAC's active site and chelate zinc, resulting in termination of substrate deacetylation (Newkirk et al. 2009). See FIG. 1.

To further define largazole's pharmacophore, it appears that upon its entry into the cytoplasm of the cell, the thioester moiety is rapidly hydrolyzed to produce the free thiol group, which can interact with the zinc ion at the bottom of the HDAC pocket and inhibit the enzymatic activity.

To validate that the largazole thiol is the reactive species, various exemplary thiol derivatives were prepared and assessed its biochemical potency in tumor cell growth inhibition and in cellular or in vitro HDAC inhibition assays. These findings indicate that the thiol analogue has similar HDAC inhibition using compound-treated cellular extracts (Bowers et al. 2008; Ying et al. 2008a; Ying et al. 2008b). In in vivo experiments where cells are treated with largazole or the largazole thiol, the parent molecule exhibited higher potency with respect to HDAC inhibition ($IC_{50}$ of 51 nM vs. 209 nM for the thiol metabolite) (Ying et al. 2008a).

With respect to antiproliferative activity, conflicting datasets were presented by two groups: Ying et al. showed that largazole and its thiol analogue exhibited similar antigrowth activity in HCT116 cells with $GI_{50}$ values of 44 and 38 nM, respectively (Ying et al. 2008b). The Williams group utilized a series of melanoma cell lines to demonstrate that largazole has a consistent superior potency ($IC_{50}$ of 45-315 nM) compared to its thiol metabolite ($IC_{50}$ of 380-2600 nM) and attributed the difference in cytotoxicity to the superior permeability of the thioester largazole (Bowers et al. 2008). To measure the deacetylase activity in vitro, purified full length HDAC proteins from class I and class II were incubated with a fluorophore-conjugated substrate and largazole or the largazole thiol. The results not only show that largazole itself is a much weaker HDAC inhibitor when compared to the reduced (thiol) version but also indicate a pronounced preference of largazole for HDACs 1, 2, and 3 over HDAC6 (Bowers et al. 2008). To account for this lack of difference in cellular-base assays, it is possible that the thioester is cleaved under the experimental conditions.

In addition, since hydroxyls (—OH) do not chelate zinc, a replacement of —SH with —OH impeded the toxic effect as well as inhibitory activity in HDAC assay (Bowers et al. 2008); (Ying et al. 2008a)). Taken together, the thiol is indispensable for both activities. As a result, one may speculate that inhibition of HDAC promotes its antitumor effect. From a biosynthesis point of view, nature produced largazole as a prodrug rather than as a target reactive species to increase its stability and to protect it from unwanted oxidation (Ying et al. 2008b). Interestingly, an analogous protect-and-liberate mechanism has been observed in a natural substance, FK228 (Shigematsu et al. 1994; Ueda et al. 1994a; Ueda et al. 1994b). This distinctive cyclic compound contains a disulfide bond which is hydrolyzed by glutathione reductase to butenyl thiol which is capable of extending toward the zinc residue to terminate HDAC activity. (See FIG. 1 and Furumai et al. 2002).

A series of analogues were prepared to evaluate the optimal length of the octanoyl chain since it is the linker that is inserted into the HDAC pocket to chelate the zinc, which results in attenuation of HDAC biological activity. It is believed that largazole as well as FK228 incorporate a four-atom linker between the macrocycle and the zinc-binding group. A macrocycle that lacks the entire octanoyl chain can neither inhibit HDACs nor does it have any toxic activity in cells, which further authenticates the importance of the thiol group in the role of largazole as an HDAC inhibitor. Neither shortening nor lengthening of the aliphatic chain is an advantageous structural modification as measured by in vivo and in vitro HDAC assays as well as by cell viability assay against the HCT116 colon cancer cell line. (See Table 2). These results suggest that the natural length of the largazole tail is optimal (Ying et al. 2008a; Ying et al. 2008b; and Newkirk et al. 2009). Furthermore, two changes within the cap region were investigated and reported by Leusch and associates: a substitution of valine to alanine and a largazole epimer (17R) (Ying et al. 2008a). The Val-, Ala-compound showed a 2-fold decrease in all inhibitory activities when compared to largazole, indicating that the valine residue can be easily interchanged. An epimer analogue behaved poorly as an HDAC inhibitor, alluding to the importance of the S— configuration at position C17 (Ying et al. 2008a). Recently, additional structure activity relationship studies on largazole have been performed by Zeng et al. (Zeng et al. 2010), where they replaced valine with leucine and phenylalanine and observed that the inhibitory activity against several cancer cell lines was slightly decreased (e.g., $GI_{50}$ for largazole was 80 nM while 560 nM and 260 nM was measured for Leu 1 and Phe 1, respectively, in HCT 116 cells). Interestingly, when valine was exchanged for tyrosine, which resulted in lowering the potency against cancer cells, the $GI_{50}$ for normal cells significantly increased, thus improving the therapeutic window (HCT-116: $GI_{50}$ of 0.39 μM; A549: $GI_{50}$ of 1.46 μM) over the normal cell lines (HEK293: $GI_{50}$ of 100 μM; HLF: $GI_{50}$ of 100 μM, while largazole's $GI_{50}$ in HEK293 was 1.36 μM and 0.98 μM in HLF cells). As a result, it was suggested that modifying largazole with Tyr could force the compound to opt for HDACs in cancer instead of normal cells (Zeng et al. 2010).

Macrocyclic HDAC inhibitors such as largazole have potential as a tool for studying the biology of HDACs while at the same time, due to largazole's preference towards killing cancer cells vs. normal cells, offering significant promise as a cancer therapeutic (i.e., comprises a large therapeutic window). The attractiveness of largazole also resides in the fact that it is highly selective towards the class I deacetylases, a feature rarely observed in HDAC inhibitors.

The pharmaceutical compositions of the invention can take any suitable form for the desired route of administration. Where the composition is to be administered orally, any suitable orally deliverable dosage form can be used, including without limitation tablets, capsules (solid or liquid filled), powders, granules, syrups and other liquids, elixirs, inhalants, troches, lozenges, and solutions. Injectable compositions or i.v. infusions are also provided in the form of solutions, suspensions, and emulsions. In a particular embodiment, the compositions are administered orally. In an exemplary embodiment, the oral dose range is 0.05 to 40 mg/kg, such as 0.1 to 30 mg/kg, such as 1 to 30 mg/kg, such as 2 to 20 mg/kg, such as 5 to 20 mg/kg, such as 10 to 15 mg/kg.

In an exemplary embodiment, a pharmaceutical composition according to the present invention may contain one or more additional therapeutic agents, for example, to increase efficacy or to decrease undesired side effects. In a particular embodiment, the pharmaceutical composition further contains one or more additional therapeutic agents useful to treat or inhibit a disease mediated directly or indirectly by HDAC. Examples of such agents include, without limitation, agents to treat or inhibit cancer, Huntington's disease, cystic fibrosis, liver fibrosis, renal fibrosis, pulmonary fibrosis, skin fibrosis, rheumatoid arthritis, diabetes or heart failure.

In a specific embodiment, the additional therapeutic agent to be included is an anti-cancer agent. Examples of anti-cancer agents include, but are not limited to, alkylating agents such as cyclophosphamide, dacarbazine and cisplatin; anti-metabolites such as methotrexate, mercaptopurine, thioguanine, fluorouracil and cytarabine; plant alkaloids such as vinblastine and paclitaxel; antitumor antibiotics such as doxorubicin, bleomycin and mitomycin; hormones/anti-hormones such as prednisone, tamoxifen and flutamide; other types of anticancer agents such as asparaginase, rituximab, trastuzumab, imatinib, retinoic acid and derivatives, colony stimulating factors, amifostine, camptothecin, topotecan, thalidomide analogs such as lenalidomide, CDK inhibitors, proteasome inhibitors such as Velcade and other HDAC inhibitors.

In another embodiment, the present invention provides a method of inhibiting or treating diseases arising from abnormal cell proliferation and/or differentiation in a subject in need thereof, comprising administering to the subject a therapeutically effective amount of one or more compounds according to the present invention. In one embodiment, the method of inhibiting or treating disease comprises administering to a subject in need thereof, a composition comprising an effective amount of one or more compounds of the invention and a pharmaceutically acceptable carrier. The composition to be administered may further contain a therapeutic agent such as anti-cancer agent.

The compounds of the invention are defined herein by their chemical structures and/or chemical names and are generally listed according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is intended to be determinative of the compound's identity.

Compounds of Formula I of the present invention are synthesized according the generic scheme that is Scheme I:

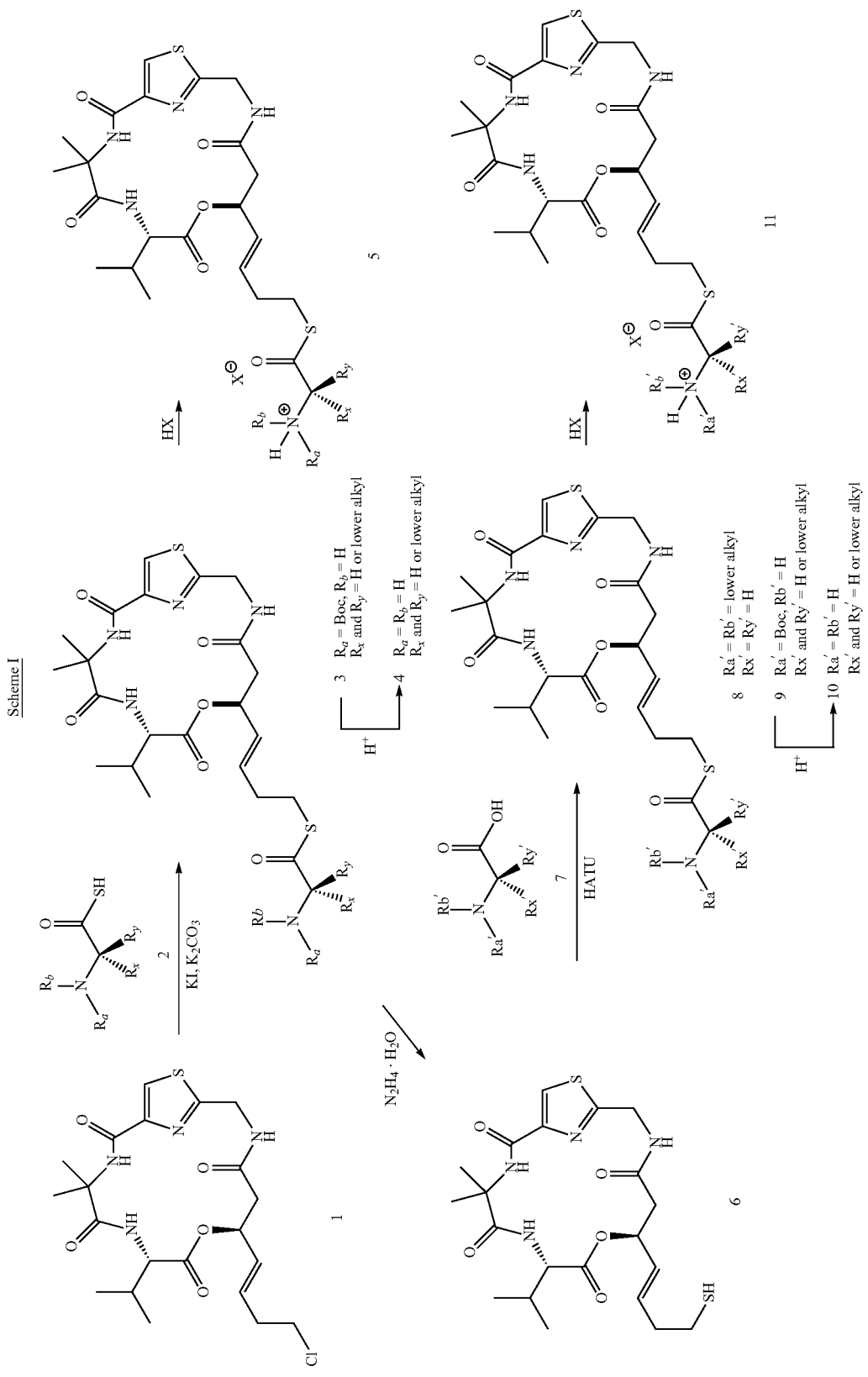

Intermediate chloride 1 can be prepared by the method described in published PCT application WO 2015/183897. Thioacid intermediates of general Formula 2 and thioester intermediates of general Formula 3 can be synthesized by well-known methods available in the art. Coupling of 1 and 2 in the presence of abase (such as potassium carbonate) and potassium iodide provides the corresponding thioester intermediate 3. Boc deprotection of 3 with an acid (such as trifluoroacetic acid) provides the primary amine 4. Salt formation by treatment of 4 with an appropriate acid then provides the ammonium salt 5. Alternatively, 3 can be hydrolyzed with a reducing agent (such as hydrazine hydrate) to give the corresponding thiol 6 which is then reacted with carboxylic acid 7 using a coupling agent (such as HATU) to give the corresponding thioester 8. In the event that the carboxylic acid 7 contains a Boc protecting group, the resulting intermediate compound 9 can be deprotected with an acid (such as trifluoroacetic acid) to give the primary amine 10. Salt formation by treatment with an appropriate acid then provides the ammonium salt 11.

EXAMPLES

The following examples are provided for illustrative purposes only and are not intended to limit the scope of the invention.

Example 1: Preparation of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate Hydrochloride

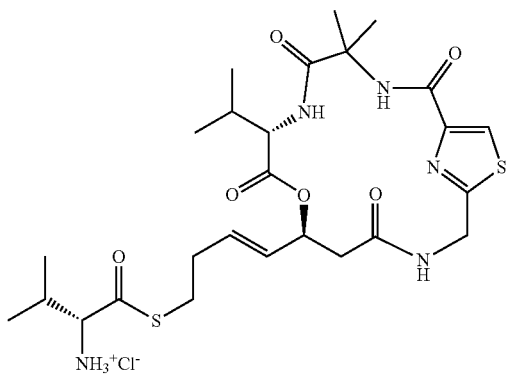

Step 1: Preparation of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate. (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone (15 g, 0.03 mol), (R)-2-((tert-butoxycarbonyl)amino)-3-methylbutanethioic S-acid (12.5 g, 0.06 mol), K$_2$CO$_3$ (11.2 g, 0.09 mol), and KI (0.89 g, 0.006 mol) were dissolved in 150 mL of acetonitrile and the resulting mixture was warmed to 60-65° C. and stirred under nitrogen. After 16 hours, the mixture was cooled to 20° C., 300 mL of water was added, and the resulting suspension was extracted with ethyl acetate (2×200 mL). The combined organic phases were dried with anhydrous sodium sulfate, filtered and concentrated. The residue was purified by flash column chromatography (elution with ethyl acetate/petroleum ether=1/1 to 4/1) to give (R)—S-((E)-4-((7S,10S)-7-isopropyl-4,4-dimethyl-2,5,8,12-tetraoxo-9-oxa-16-thia-3,6,13,18-tetraazabicyclo[13.2.1] octadeca-1(17),15(18)-dien-10-yl)but-3-en-1-yl) 2-((tert-butoxycarbonyl)amino)-3-methylbutanethioate (17.0 g, 80% yield).

Step 2: Preparation of (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate hydrochloride. (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate (1.7 g, 0.025 mol) was dissolved in 150 mL of dichloromethane and trifluoroacetic acid (22.5 mL) was added at 10° C. After stirring at 10° C. for 4 hours under nitrogen, the mixture was concentrated to dryness and the residue was dissolved in 100 mL of ethyl acetate and treated with 10 mL of 4M HCl/ethyl acetate solution. The mixture was then treated with petroleum ether (100 mL) and the resulting white solid was collected by filtration and dried to give (R)—S-((E)-4-((7S,10S)-7-isopropyl-4,4-dimethyl-2,5,8,12-tetraoxo-9-oxa-16-thia-3,6,13,18-tetraazabicyclo [13.2.1] octadeca-1(17),15(18)-dien-10-yl)but-3-en-1-yl) 2-amino-3-methylbutanethioate hydrochloride (0.40 g, 26% yield). Mass Spec (m/z): 582.8 (M+1).

Example 2: Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate Hydrochloride

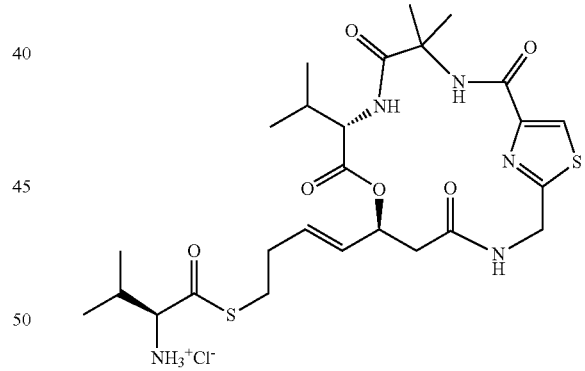

Step 1: (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate. (7S,10S)-10-((E)-4-chlorobut-1-en-1-yl)-7-isopropyl-4,4-dimethyl-9-oxa-16-thia-3,6,13,18-tetraazabicyclo[13.2.1] octadeca-1(17),15(18)-diene-2,5,8,12-tetraone (40 g, 0.0825 mol), (S)-2-((tert-butoxycarbonyl)amino)-3-methylbutanethioic S-acid (38.5 g, 0.165 mol), K$_2$CO$_3$ (34.1 g, 0.247 mol), and KI (2.7 g, 0.0163 mol) were dissolved in 400 mL of acetonitrile and stirred at 60-65° C. under nitrogen for 20 hours. The mixture was cooled to 20° C., water (300 mL) was added and the resulting suspension was extracted with ethyl acetate (2×200 mL). The organic phases were combined, dried with anhydrous sodium sulfate, filtered and concentrated. The residue was purified by flash column chromatography (elution with ethyl acetate/petroleum ether=1/1 to 4/1) to give (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate (49.8 g, 89% yield).

Step 2: (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate hydrochloride. (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate (47.8 g, 0.07 mol) was dissolved in dichloromethane (400 mL) and trifluoroacetic acid (65 mL) was added dropwise at 10 to 20° C. while stirring under nitrogen. After the addition, the mixture was stirred at 15 to 20° C. for 3 hours at which time an additional aliquot of trifluoroacetic acid (20 mL) was added and stirring at 15 to 20° C. was continued for an additional 1.5 hours. The solution was then concentrated under vacuum to near dryness and the residue dissolved in ethyl acetate (250 mL). 20 mL of 4M HCl/ethyl acetate solution was then added while stirring at a temperature between 10 to 15° C. resulting in the formation of a slurry. 250 mL n-heptane was then added and the solids were filtered, rinsed with n-heptane and dried in vacuo to give (S)—S-((E)-4-((7S,10S)-7-isopropyl-4,4-dimethyl-2,5,8,12-tetraoxo-9-oxa-16-thia-3,6,13,18-tetraazabicyclo[13.2.1] octadeca-1(17),15(18)-dien-10-yl)but-3-en-1-yl) 2-amino-3-methylbutanethioate hydrochloride as a white solid which contained some residual heptane. (49.0 g, 100% yield). Mass Spec (m/z): 582.8 (M+1)

Example 3: Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate Benzenesulfonate The product of Example 2, step 1 ((S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate) (1 eq.) was dissolved in acetonitrile (10 vol) at 20-25° C. and the mixture was treated with benzenesulfonic acid (3 eq.). After stirring at room temperature for 5 hours, the solvent was removed by decanting, the residual oil was treated with THF (5 vol), and the resulting mixture was stirred over night at room temperature. The resulting white solid was collected by filtration and dried in vacuo to give (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate (90% yield; 98% purity). $^1$HNMR (d$_6$-DMSO) δ: 0.56 to 0.57 (m, 3H), 0.76 to 0.78 (m, 3H), 0.92 to 0.94 (m, 3H), 0.96 to 0.98 (m, 3H), 1.45 to 1.48 (m, 3H), 1.70 to 1.72 (m, 3H), 2.07 to 2.16 (m, 2H), 2.27 to 2.28 (m, 2H), 2.93 to 2.95 (m, 1H), 2.94 to 2.95 (m, 1H), 2.97 to 3.1 (m, 1H), 4.13 to 4.15 (m, 1H), 4.28 to 4.33 (1H), 4.92 to 5.0 (m, 1H), 5.61 to 5.64 (m, 3H), 7.29 to 7.32 (m, 3H), 7.57 to 7.60 (m, 2H), 7.88 to 7.92 (m, 1H), 8.17 (s, 1H), 8.32 (s, 3H), 8.48 to 8.50 (m, 1H).

Example 4: (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate Oxalate

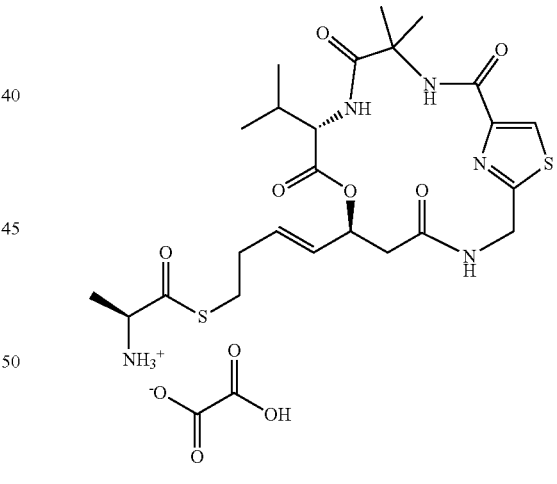

Step 1: Preparation of (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone. To a solution of (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone (1:1) hydrochloride from Example 2 (1.5 g, 2.43 mmol) in acetonitrile (30 mL) was added N$_2$H$_4$.H$_2$O (620 mg, 12.15 mmol) in one portion at room temperature. The mixture was stirred at room temperature under nitrogen for 2 hours at which time acetone (20 mL)

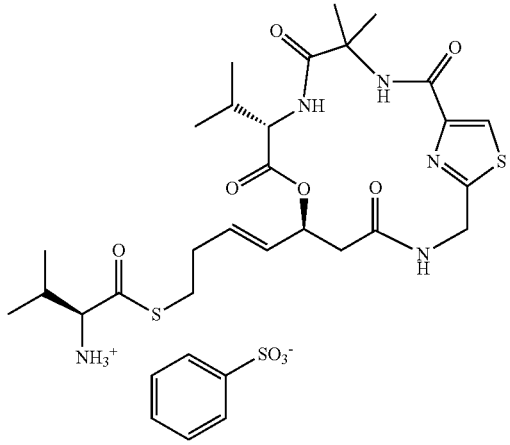

was added. The mixture was concentrated and the residue dissolved in dichloromethane (50 mL). The organic layer was washed with 1M citric acid solution (3×20 mL), saturated sodium bicarbonate solution (2×20 mL) and brine (20 mL). The organic layer was dried over anhydrous sodium sulfate, filtered and concentrated to afford (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone (0.90 g) as colorless oil which was used directly in the next step.

Step 2: Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)propanethioate. To a mixture of (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone (450 mg, 0.93 mmol) in dichloromethane (30 mL) was added HATU (530 mg, 1.40 mmol), diisopropylethyl amine (486 µL, 2.33 mmol) and (S)-2-((tert-butoxycarbonyl)amino)propanoic acid (194 mg, 1.03 mmol). The mixture was stirred at room temperature under nitrogen for 16 hours at which time 1M aqueous ammonium chloride (20 mL) was added. The aqueous phase was extracted with dichloromethane (2×20 mL) and the combined organic phases were washed with saturated sodium bicarbonate solution (20 mL), brine (20 mL), dried with anhydrous $Na_2SO_4$, filtered and concentrated. Purification of the residue by flash silica gel chromatography (dichloromethane/methanol=40/1) afforded (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)propanethioate as yellow oil (310 mg, 51% yield).

Step 3: Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate hydrochloride. To a solution of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)propanethioate (300 mg, 0.46 mmol) in dichloromethane (30 mL) at 0° C., was added trifluoroacetic acid (157 mg, 1.38 mmol) in three equal portions. The mixture was stirred under nitrogen at 0° C. for 4 hours and then concentrated. The residue was dissolved in $H_2O$ (10 mL), cooled to 0° C. and oxalic acid (41 mg, 0.46 mmol) was added. The mixture was stirred at 0° C. for 30 minutes and then placed on a lyophilizer to obtain (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate (218 mg, 74% yield) which contained small but varying amounts of the corresponding trifluoroacetate salt as evidenced by $^{19}F$ NMR. Mass Spec (m/z): 554.1 (M+1)

Example 5: (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate Oxalate

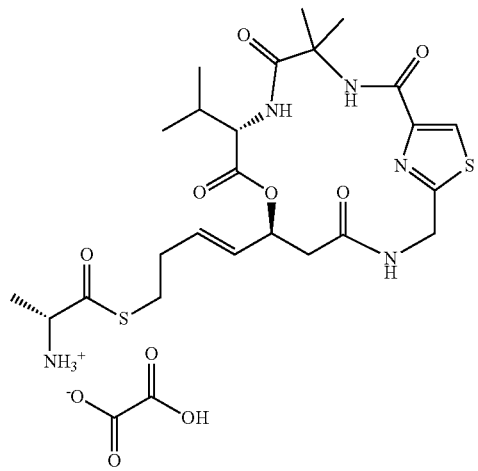

The product was prepared using the protocol described for Example 3. (R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-aminopropanethioate oxalate (21 mg, 55% yield) was isolated as white solid which contained small but varying amounts of the corresponding trifluoroacetate salt as evidenced by $^{19}F$ NMR. Mass Spec (m/z): 554.1 (M+1).

Example 6: S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate

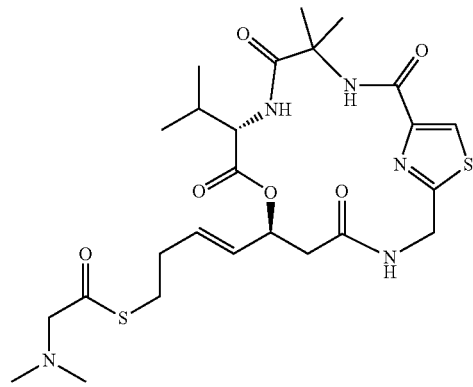 [SMILES: CC(C)[C@@H]1NC(=O)C(C)(C)NC(=O)c2csc(n2)CNC(=O)C[C@@H](/C=C/CCSC(=O)CN(C)C)OC1=O]

Preparation of S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate. To a mixture of (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone (500 mg, 1.04 mmol) and 2-(dimethylamino)acetic acid (117 mg, 1.04 mmol) in dichloromethane (20 mL) at room temperature was added HATU (583 mg, 1.56 mmol) and DIPEA (550 μL, 3.12 mmol). The mixture was stirred at room temperature under nitrogen for 16 hours at which time 20 mL of saturated ammonium chloride solution was added. The layers were separated and the aqueous phase was extracted with dichloromethane (2×20 mL). The combined organic layers were washed with saturated sodium bicarbonate solution (20 mL), brine (20 mL), dried with anhydrous Na$_2$SO$_4$, filtered and concentrated. Two step purification, first using silica gel chromatography (dichloromethane/methanol=10/1) followed by preparative HPLC afforded S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate (170 mg, 29% yield) as white solid. Mass Spec (m/z): 568.2 (M+1).

Preparative HPLC Purification Conditions:
Instrument: SHIMADZU preparative HPLC system
Mobile phase: A: 0.01M NH$_4$HCO$_3$ in H$_2$O; ACN
Column: Luna C18 250*30, 10 um, 100 A
Flow rate: 80 ml/min
Monitor wavelength: 220 and 254 nm
Gradient:

| Time | B % |
|---|---|
| 0.00 | 30 |
| 25.0 | 60 |
| 25.10 | 100 |
| 30.10 | 30 |

Example 7: S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl) pyridine-3-carbothioate

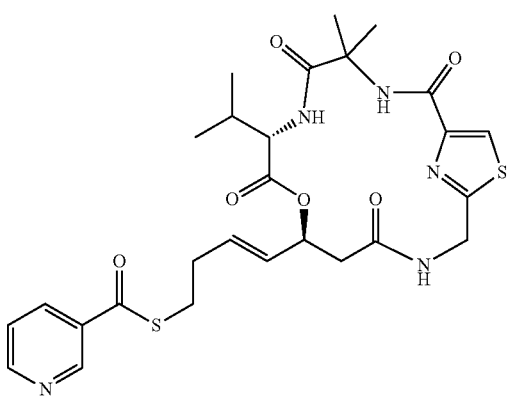 [SMILES: CC(C)[C@@H]1NC(=O)C(C)(C)NC(=O)c2csc(n2)CNC(=O)C[C@@H](/C=C/CCSC(=O)c2cccnc2)OC1=O]

To a mixture of (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone from Example 3 (300 mg, 0.62 mmol) and nicotinic acid (76 mg, 0.62 mmol) in dichloromethane (20 mL) at room temperature was added HATU (304 mg, 0.80 mmol) and DIPEA (261 μL, 1.5 mmol). The mixture was stirred at room temperature under nitrogen for 16 hours at which time saturated ammonium chloride solution (20 mL) was added. The layers were separated and the aqueous phase was extracted with dichloromethane (2×20 mL). The combined organic layers were washed with saturated sodium bicarbonate solution (20 mL), brine (20 mL), dried with anhydrous Na$_2$SO$_4$, filtered and concentrated. Purification using silica gel chromatography (dichloromethane/methanol=10/1) afforded S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-(dimethylamino)ethanethioate (116 mg, 32% yield) as white solid. Mass Spec (m/z): 558.1 (M+1).

Example 8: 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic Acid

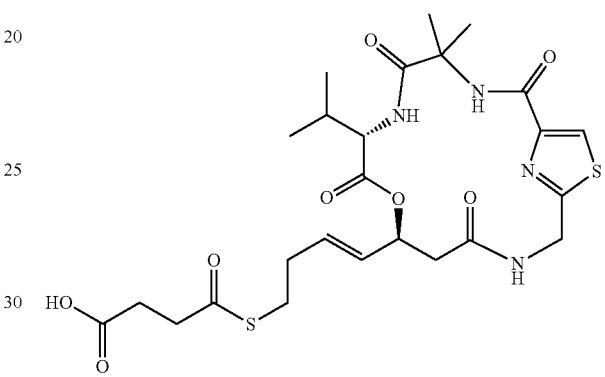

To a stirred solution of tetrahydrofuran-2,5-dione (74.65 mg, 0.75 mmol) and DMAP (9.11 mg, 76 umol) in a mixture of pyridine (200 uL) and acetonitrile (2.00 mL) at 25° C. under N$_2$, was added (7S,10S)-7-isopropyl-10-((E)-4-mercaptobut-1-en-1-yl)-4,4-dimethyl-9-oxa-16-thia-3,6,13,18-tetraazabicyclo[13.2.1]octadeca-1(17),15(18)-diene-2,5,8,12-tetraone from Example 3 (360 mg, 0.75 mmol). The colorless solution was stirred at 25° C. for 15 h and then concentrated. The crude product was purified by preparative HPLC (HCO$_2$H system) and then lyophilized to give 5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid (180 mg, 41% yield) as white solid. Mass Spec (m/z): 583.3 (M+1).

Preparative HPLC Purification Conditions:
Instrument: Gilson 281 semi-preparative HPLC system
Mobile phase: A: FA/H$_2$O=0.1% v/v; B: ACN
Column: YMC-Actus Triart C18 150*30 5 um
Flow rate: 25 mL/min
Monitor wavelength: 220 and 254 nm
Gradient:

| Time | B % |
|---|---|
| 0.00 | 20 |
| 8.0 | 45 |
| 10.0 | 45 |
| 10.2 | 100 |
| 11.7 | 100 |
| 11.9 | 20 |
| 13.9 | 20 |

Example 9: Tumor Growth Inhibition Using HCT-116 Xenograft

Figure 2:
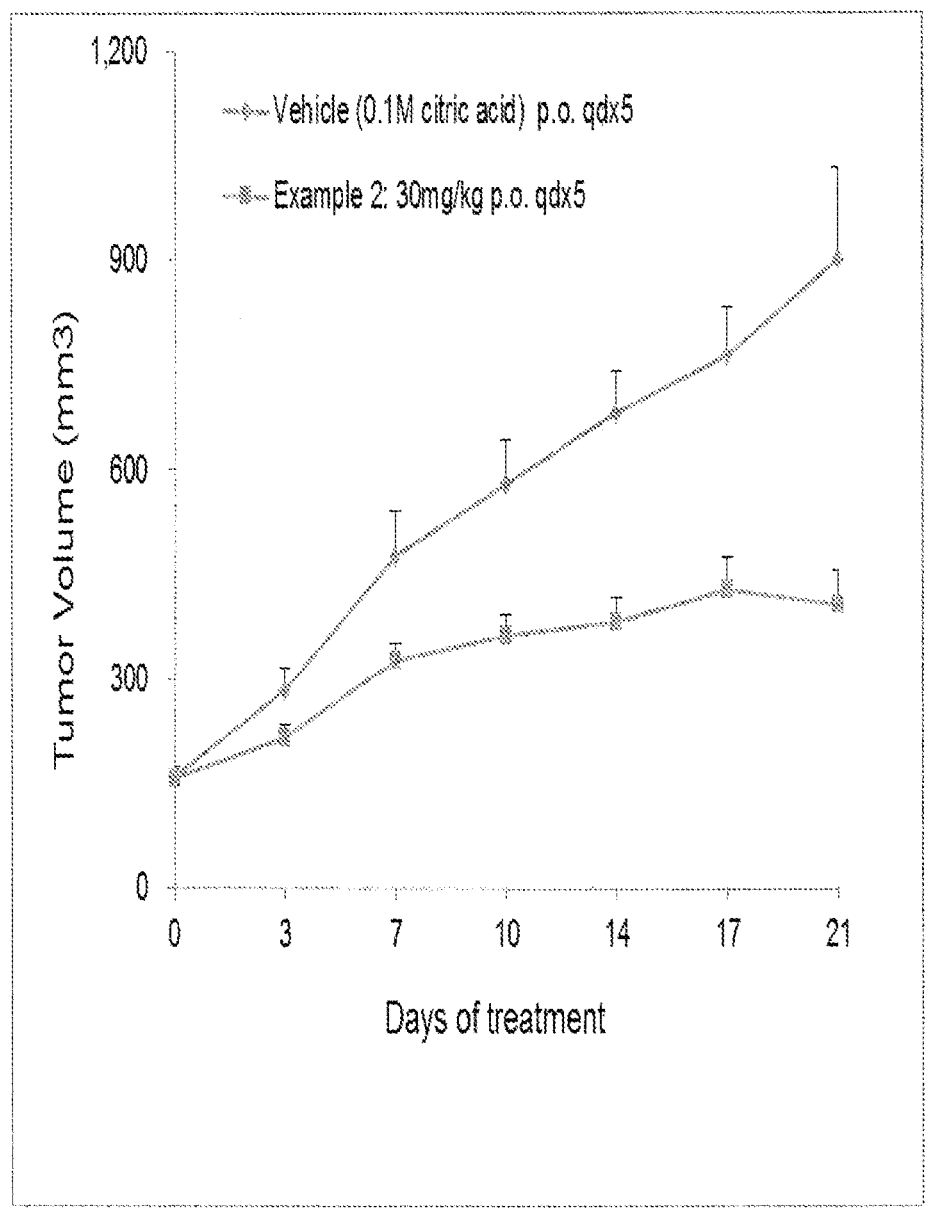
FIG. 2 depicts the results of a tumor growth inhibition study in nude mice using a HCT-116 colorectal cancer xenograft exposed to the compound of Example 2 at 30 mg/kg p.o., qdx5.
Figure 3:
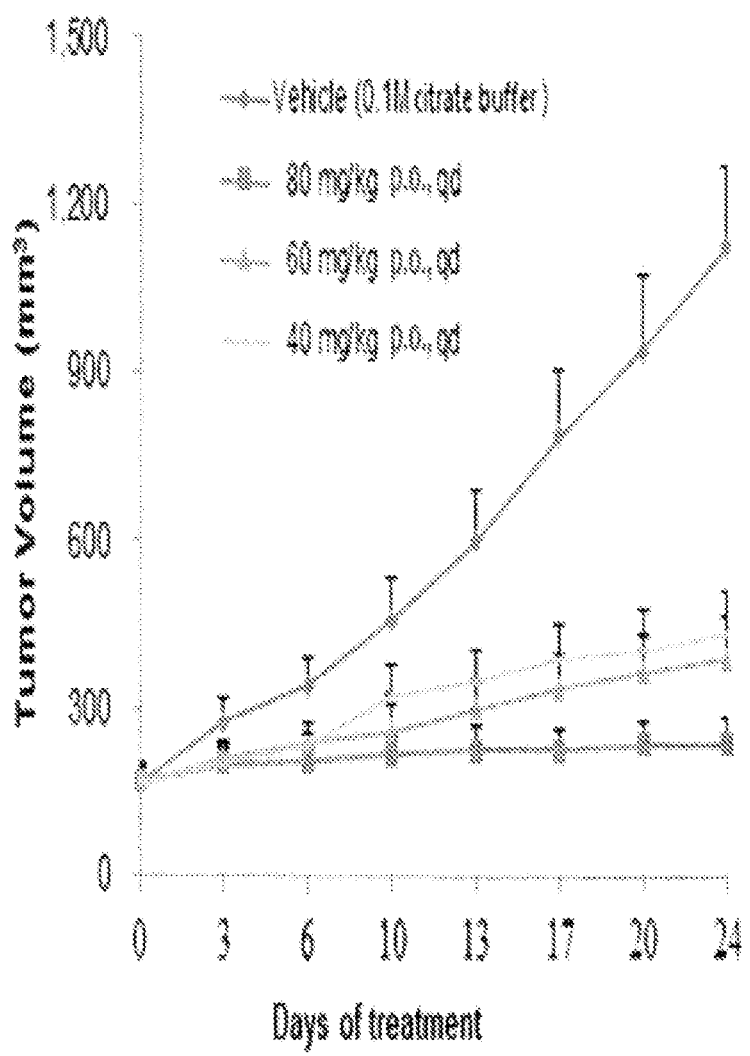
FIG. 3 depicts the results of a tumor growth inhibition study in nude mice using a HCT-116 colorectal cancer xenograft exposed to the compound of Example 3 at 40 mg/kg p.o., qd; at 60 mg/kg p.o., qd; and at 80 mg/kg p.o., qd.
Figure 4:
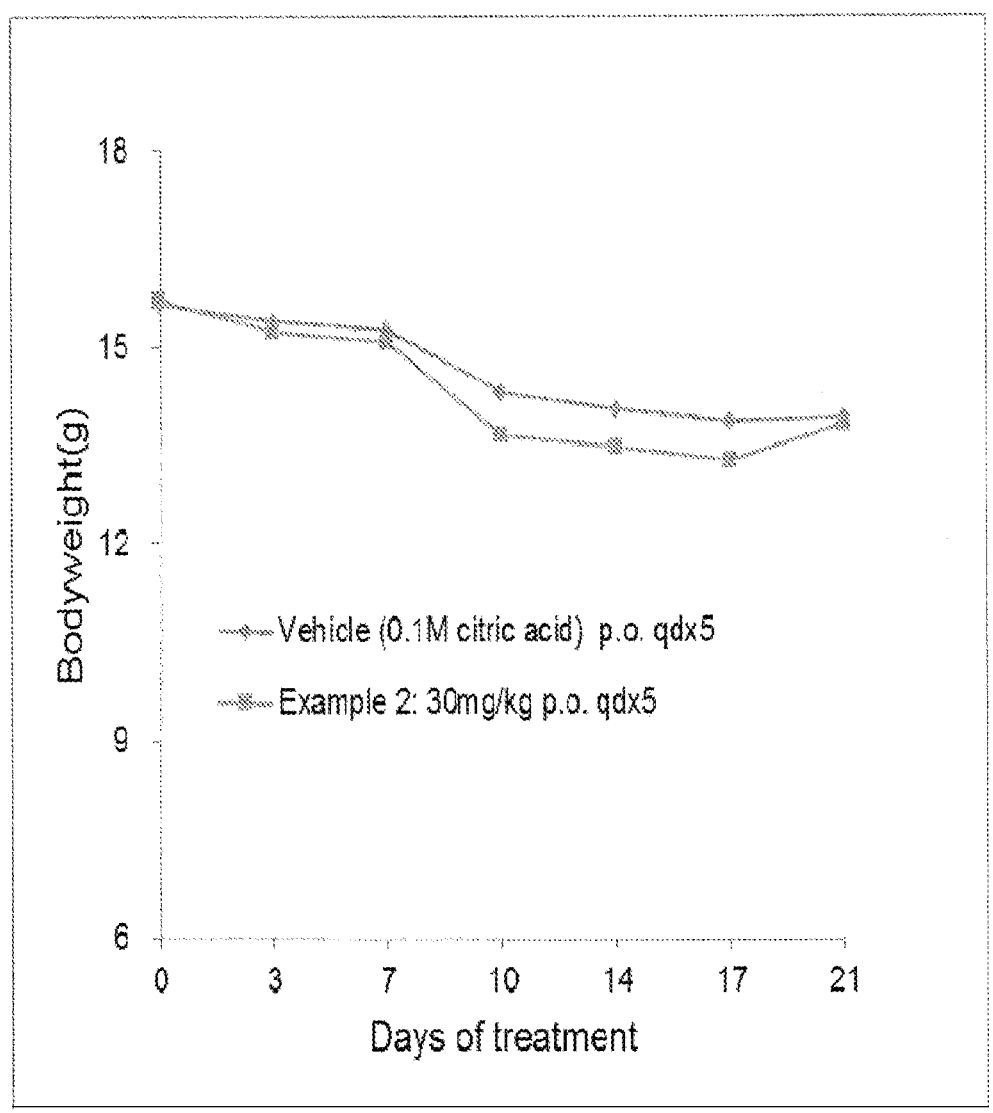
FIG. 4 depicts observed animal weight measurements resulting from the study described in FIG. 2.
Figure 5:
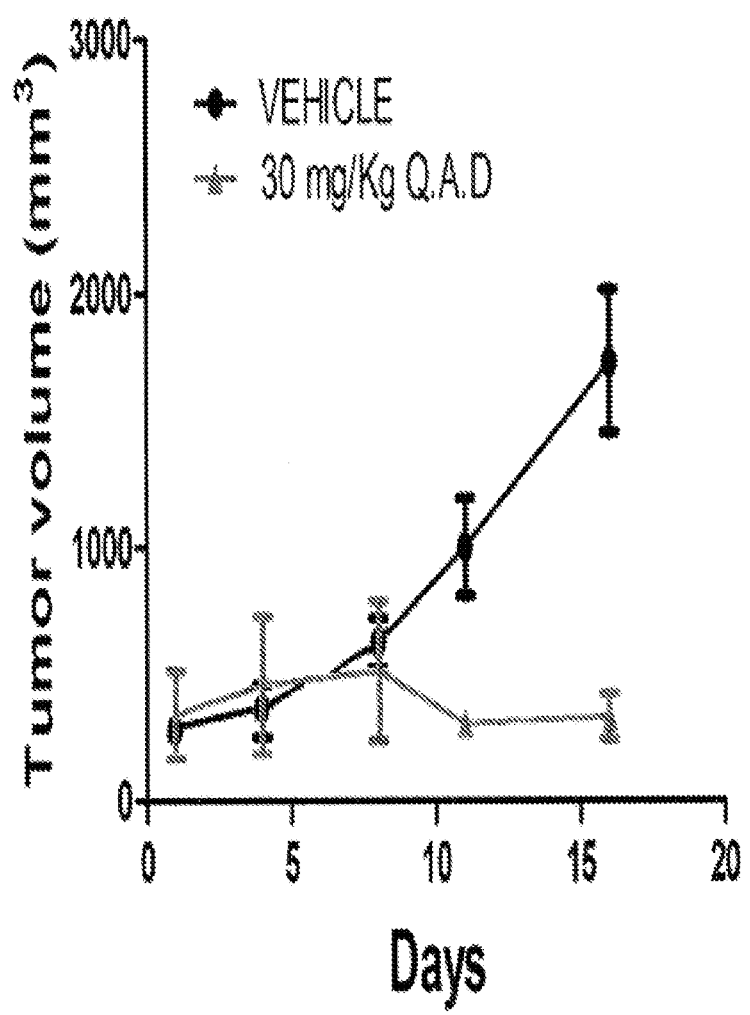
FIG. 5 depicts the results of a tumor growth inhibition study in humanized mice using a patient-derived colorectal cancer tumor exposed to the compound of Example 3.

Xenograft experiments were conducted with female BALB/c nude mice (Beijing Vital River Laboratory Animal Technology Co., Ltd., Beijing) that were 6 to 8 weeks old. Subcutaneous HCT-116 CRC xenografts were established and allowed to grow until they reached approximately 150 mm$^3$ (day 0). Animals were randomized to treatment groups: vehicle and the compound of Example 1 (n=5 per group). The compound of Example 2 was administered at 60 mg/kg by oral gavage once daily (qd) for 5 consecutive days a week. See FIG. 2. Two perpendicular diameters of tumors were measured every 3-4 days with a digital caliper by the same investigator. Tumor volume was calculated according to the following formula: TV (mm$^3$)=(length [mm]×(width [mm]2)/2. Animal body weight was measured every 3-4 days as an index of toxicity. See FIG. 4. A similarly structured study was conducted with the compound of Example 3 as shown in FIGS. 3 and 5.

Table 1 depicts aqueous solubility values at two different pH levels for selected compounds and Table 2 shows pharmacokinetic data in rat.

TABLE 1

| | Solubility (mg/mL) | | | | | |
|---|---|---|---|---|---|---|
| pH | Example 1 | Example 2 | Example 3 | Example 4 | Example 5 | Example 6 |
| 3 | 8.67 | 12.32 | 7.50 | 15.39 | 45.45 | 2.45 |
| 6 | 10.51 | 18.04 | — | 25.19 | 41.75 | 2.32 |

TABLE 2

| | Rat PK (p.o.) | | | |
|---|---|---|---|---|
| Compound | $t_{1/2}$ (hr) | Tmax (hr) | Cmax (ng/mL) | AUCINF (hr*ng/mL) |
| Example 1* | 8.53 | 0.42 | 86 | 257 |
| Example 2* | 8.23 | 0.48 | 123 | 267 |
| Example 3** | 12.40 | 0.6 | 253 | 583 |
| Example 4* | 6.09 | 1.0 | 51 | 176 |
| Example 5* | | | Not Determined | |
| Example 6* | 5.86 | 0.83 | 107 | 272 |
| Example 7* | 6.88 | 0.33 | 150 | 240 |

*10 mg/kg; Vehicle (0.02N HCl sol.)
**15 mg/kg; Vehicle (0.1N citrate buffer)
Cmax = maximum plasma concentration
Tmax = time to Cmax
AUCINF = area under the plasma concentration versus time curve from zero to infinity The data shown in Table 1 shows the suitable aqueous solubility values at two different pH levels for the compounds of Examples 1 to 6 as representative of the thioester prodrugs of the invention. Table 2 demonstrates that the thioester prodrugs of the invention, represented by the compounds of Examples 1 to 7, also exhibit unexpectedly good pharmacokinetic (PK) properties in rat when dosed orally at 10 or 15 mg/kg.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entireties by reference.

REFERENCES

Bowers, A., West, N., Taunton, J., Schreiber, S. L., Bradner, J. E., and Williams, R. M. 2008. Total synthesis and biological mode of action of largazole: a potent class I histone deacetylase inhibitor. J Am. Chem. Soc. 130(33): 11219-11222.

Furumai, R., Matsuyama, A., Kobashi, N., Lee, K.-H., Nishiyama, M., Nakajima, H., Tanaka, A., Komatsu, Y., Nishino, N., Yoshida, M., and Horinouchi, S. 2002. FK228 (depsipeptide) as a natural prodrug that inhibits class I histone deacetylases. Cancer Res. 62(17): 4916-4921.

Ghosh, A. K. and Kulkami, S. 2008. Enantioselective total synthesis of (+)-largazole, a potent inhibitor of histone deacetylase. Org. Lett. 10(17): 3907-3909.

Hang, H. C. and Bertozzi, C. R. 2001. Chemoselective approaches to glycoprotein assembly. Accounts of Chemical Research 34(9): 727-736.

Kiick, K. L., Saxon, E., Tirrell, D. A., and Bertozzi, C. R. 2002. Incorporation of azides into recombinant proteins for chemoselective modification by the Staudinger ligation. Proc. Natl. Acad. Sci. U.S.A. 99(1): 19-24.

Koho, K. T. 1991. In (ed. F.P.C. Ltd).

Lemieux, G. A. and Bertozzi, C. R. 1998. Chemoselective ligation reactions with proteins, oligosaccharides and cells. Trends in Biotechnology 16(12): 506-513.

Marks, P. A. 2010. The clinical development of histone deacetylase inhibitors as targeted anticancer drugs. Expert Opin. Investig. Drugs 19(9): 1049-1066.

Marks, P. A. and Breslow, R. 2007. Dimethyl sulfoxide to vorinostat: development of this histone deacetylase inhibitor as an anticancer drug. Nat. Biotechnol. 25(1): 84-90.

Masuoka, Y., Shin-Ya, K., Furihata, K., Nagai, K., Suzuki, K., Hayakawa, Y., and Seto, H. 2001. Phoenistatin, a new gene expression-enhancing substance produced by *Acremonium fusigerum*. J. Antibiot. (Tokyo) 54(2): 187-190.

Minucci, S. and Pelicci, P. G. 2006. Histone deacetylase inhibitors and the promise of epigenetic (and more) treatments for cancer. Nat. Rev. Cancer 6(1): 38-51.

Nasveschuk, C. G., Ungermannova, D., Liu, X., and Phillips, A. J. 2008. A concise total synthesis of largazole, solution structure, and some preliminary structure activity relationships. Org. Lett. 10(16): 3595-3598.

Newkirk, T. L., Bowers, A. A., and Williams, R. M. 2009. Discovery, biological activity, synthesis and potential therapeutic utility of naturally occurring histone deacetylase inhibitors. Nat. Prod. Rep. 26(10): 1293-1320.

Rautio, J., Kumpulainen, H., Heimbach, T., Oliyai, R., Oh, D., Jarvinen, T., and Savolainen, J. 2008. Prodrugs: design and clinical applications. Nat. Rev. Drug Discov. 7(3): 255-270.

Seiser, T., Kamena, F., and Cramer, N. 2008. Synthesis and biological activity of largazole and derivatives. Angew. Chem. Int. Ed Engl 47(34): 6483-6485.

Shigematsu, N., Ueda, H., Takase, S., Tanaka, H., Yamamoto, K., and Tada, T. 1994. FR901228, a novel antitumor bicyclic depsipeptide produced by *Chromobacterium violaceum* No. 968. II. Structure determination. J. Antibiot. (Tokyo) 47(3): 311-314.

Taori, K., Paul, V. J., and Luesch, H. 2008. Structure and activity of largazole, a potent antiproliferative agent from the Floridian marine cyanobacterium *Symploca* sp. J. Am. Chem. Soc. 130(6): 1806-1807.

Ueda, H., Manda, T., Matsumoto, S., Mukumoto, S., Nishigaki, F., Kawamura, I., and Shimomura, K. 1994a. FR901228, a novel antitumor bicyclic depsipeptide produced by *Chromobacterium violaceum* No. 968. III. Antitumor activities on experimental tumors in mice. J. Antibiot. (Tokyo) 47(3): 315-323.

Ueda, H., Nakajima, H., Hori, Y., Goto, T., and Okuhara, M. 1994b. Action of FR901228, a novel antitumor bicyclic depsipeptide produced by *Chromobacterium violaceum* no. 968, on Ha-ras transformed NIH3T3 cells. Bioscience, Biotechnology, and Biochemistry 58(9): 1579-1583.

Ying, Y., Liu, Y., Byeon, S. R., Kim, H., Luesch, H., and Hong, J. 2008a. Synthesis and activity of largazole analogues with linker and macrocycle modification. Org. Lett. 10(18): 4021-4024.

Ying, Y., Taori, K., Kim, H., Hong, J., and Luesch, H. 2008b. Total synthesis and molecular target of largazole, a histone deacetylase inhibitor. J. Am. Chem. Soc. 130(26): 8455-8459.

Zeng, X., Yin, B., Hu, Z., Liao, C., Liu, J., Li, S., Li, Z., Nicklaus, M. C., Zhou, G., and Jiang, S. Total synthesis and biological evaluation of largazole and derivatives with promising selectivity for cancers cells. Org. Lett. 12(6): 1368-1371.

What is claimed is:

1. A method for preparing a compound of formula 10

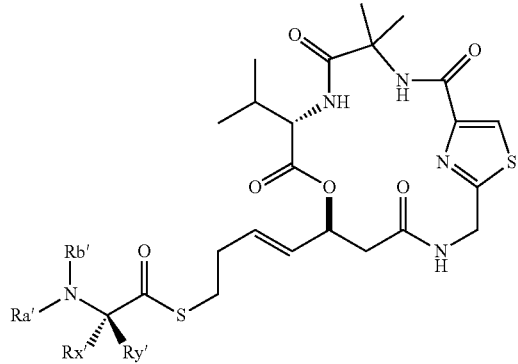

10 wherein:
Ra' and Rb' are H;
Rx' is H or lower alkyl; and
Ry' is H or lower alkyl,
the method comprising coupling of a thiol compound 6

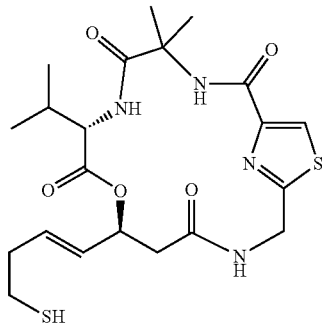

6 with a compound of formula 7

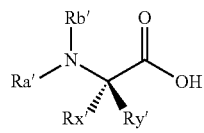

7 wherein:
Ra' is Boc;
Rb' is H;
Rx' is H or lower alkyl; and
Ry' is H or lower alkyl,
to provide a compound of formula 9

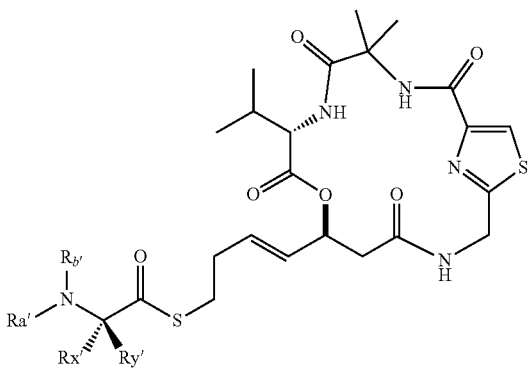

9 wherein:
Ra' is Boc;
Rb' is H;
Rx' is H or lower alkyl; and
Ry' is H or lower alkyl,
followed by deprotection of the compound of formula 9 to provide the compound of formula 10.

2. A method for preparing a compound of formula 11 by treating the compound of formula 10 of claim 1 with an acid HX

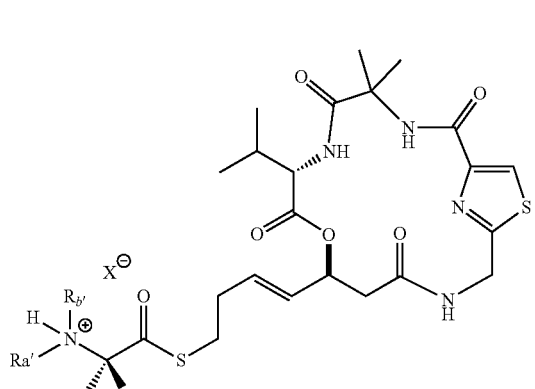

11 wherein:
Ra' and Rb' are H;
Rx' is H or lower alkyl; and
Ry' is H or lower alkyl.

3. The method according to claim 1, wherein the thiol compound 6 is prepared by reduction of a compound of formula 3 or 4

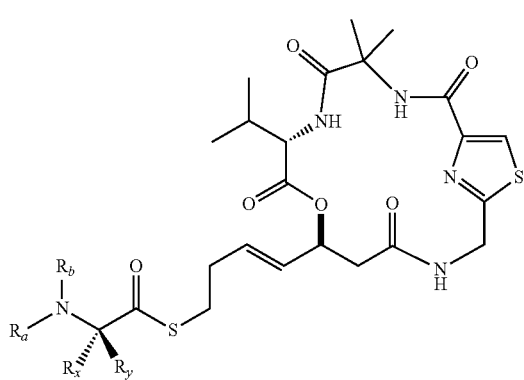

wherein for formula 3:
Ra is Boc and Rb is H;
Rx is H or lower alkyl; and
Ry is H or lower alkyl; and
wherein for formula 4:
Ra and Rb are H;
Rx is H or lower alkyl; and
Ry is H or lower alkyl.

4. The method according to claim 1, wherein the thiol compound 6 is coupled to a compound of formula 7 by treatment with HATU.

5. The method according to claim 1, wherein the compound of formula 9 is deprotected to the compound of formula 10 by treatment with trifluoroacetic acid.

6. The method according to claim 2, wherein the acid HX is selected from the group consisting of hydrochloric acid, hydrobromic acid, sulfuric acid, phosphoric acid, nitric acid, acetic acid, oxalic acid, tartaric acid, succinic acid, malic acid, fumaric acid, maleic acid, ascorbic acid, benzoic acid, tannic acid, pamoic acid, alginic acid, polyglutamic acid, methanesulfonic acid, benzenesulfonic acid, 4-nitrobenzene sulfonic acid, 4-bromobenzene sulfonic acid, toluensulfonic acid, naphthalene sulfonic acid, naphthalene disulfonic acid, and polygalacturonic acid.

7. The method according to claim 1, wherein the compound of formula 9 is selected from the group consisting of:
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)-3-methylbutanethioate;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)-3-methylbutanethioate;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)propanethioate; and
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)propanethioate.

8. The method according to claim 2, wherein compound of formula 11 is selected from the group consisting of:
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-amino-3-methylbutanethioate hydrochloride;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-amino-3-methylbutanethioate hydrochloride;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-amino-3-methylbutanethioate benzenesulfonate;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-aminopropanethioate oxalate; and
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-aminopropanethioate oxalate.

9. A compound selected from the group consisting of:
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)-3-methylbutanethioate;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)-3-methylbutanethioate;
(S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)propanethioate;
(R)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-((tert-butoxycarbonyl)amino)propanethioate;
S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)-2-(dimethylamino)ethanethioate;
S-((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)-pyridine-3-carbothioate; and
5-(((E)-4-((7S,10S,Z)-7-isopropyl-4,4-dimethyl-2,5,8,12-tetraoxo-9-oxa-3,6,13-triaza-1(4,2)-thiazolacyclotetradecaphane-10-yl)but-3-en-1-yl)thio)-5-oxopentanoic acid.

10. A pharmaceutical composition comprising the compound of claim 9 and one or more excipients.

11. The pharmaceutical composition according to claim 10, further comprising one or more anti-cancer agents.

12. The pharmaceutical composition according to claim 11, wherein the one or more anti-cancer agents are selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, amifostine, camptothecin, topotecan, thalidomide, lenalidomide, a CDK inhibitor, a proteasome inhibitor, and a HDAC inhibitor.

13. A method for treating a disease mediated by a HDAC enzyme comprising administering to a mammal in need thereof a therapeutically effective amount of the pharmaceutical composition according to claim 10, wherein the disease mediated by a HDAC enzyme is colorectal cancer.

14. A method for treating a disease mediated by a HDAC enzyme comprising administering to a mammal in need thereof a therapeutically effective amount of the pharmaceutical composition according to claim 11, wherein the disease mediated by a HDAC enzyme is colorectal cancer.

* * * * *